United States Patent [19]
Rodriguez

[11] Patent Number: 5,694,199
[45] Date of Patent: Dec. 2, 1997

[54] METHOD AND APPARATUS FOR PERFORMING AUTOMATED VISION PERFORMANCE TESTS

[76] Inventor: Edgar R. Rodriguez, 25 De Mayo 77, (4200) Santiago, Argentina

[21] Appl. No.: 670,522

[22] Filed: Jun. 27, 1996

Related U.S. Application Data

[60] Provisional application No. 60/004,595 Sep. 27, 1995.

[51] Int. Cl.⁶ .................. A61B 3/02; A61B 3/00
[52] U.S. Cl. ............... 351/223; 351/239; 351/246
[58] Field of Search .................. 351/222, 223, 351/224, 239, 244, 245, 246

[56] References Cited

U.S. PATENT DOCUMENTS

| | | | |
|---|---|---|---|
| 5,206,671 | 4/1993 | Eydelman et al. | 351/223 X |
| 5,530,492 | 6/1996 | Ron | 351/222 X |

*Primary Examiner*—Huy Mai
*Attorney, Agent, or Firm*—Frost & Jacobs

[57] ABSTRACT

An improved visual performance tester is provided which measures and stores very precise information concerning the visual sensitivity of a human eye, by use of a series of contrasting images on a computer monitor screen under a controlled-lighting environment. The tester measures the time it takes for a human patient to give the answers required by the test, thereby providing more accurate information than previously available in conventional vision testing systems. Various charts having different spatial frequencies (i.e., different sizes of bands inside a circle), different band inclinations, and different contrast characteristics are periodically displayed on the computer monitor, while the patient presses buttons (or areas) on the monitor screen to indicate his or her ability to perceive the chart images. By gradually and randomly decreasing the contrast, and/or increasing the spatial frequency, the tester can determine the patient's critical vision threshold. The test conditions are normalized in order to better compare one test result to another so that a database of "standard" human eye vision data can be accumulated for future use. After a database is established for a particular testing system, the results for an individual patient can automatically be compared to "normal" results, and the testing system's overall results in diagnosis of vision problems are superior in accuracy, precision, and range of parameters automatically measured and evaluated.

13 Claims, 23 Drawing Sheets

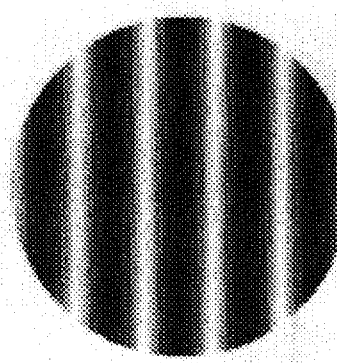 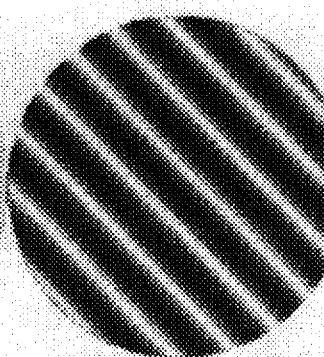 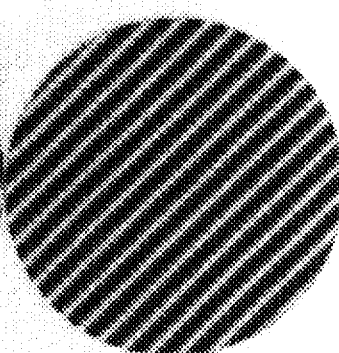
Fig. 23A          Fig. 23D          Fig. 23G
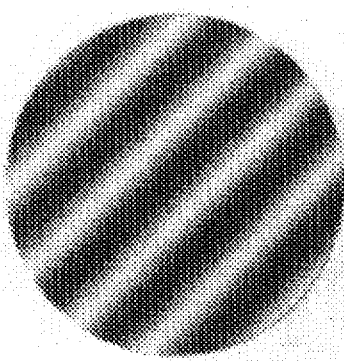 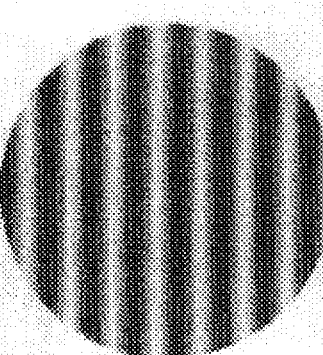 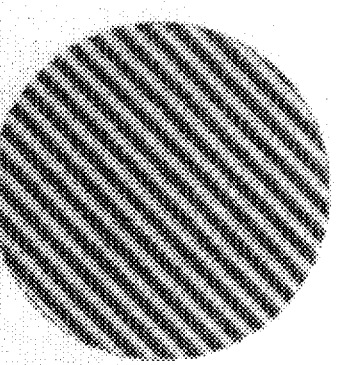
Fig. 23B          Fig. 23E          Fig. 23H
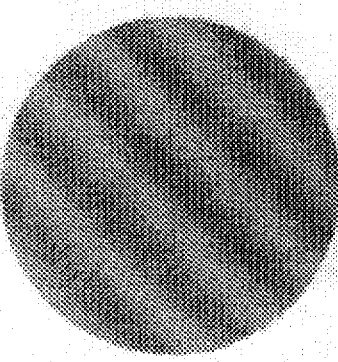 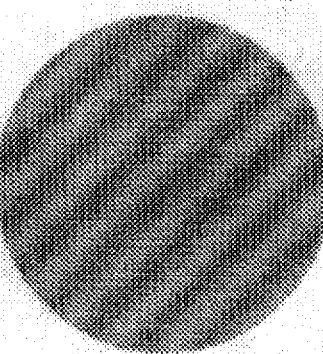 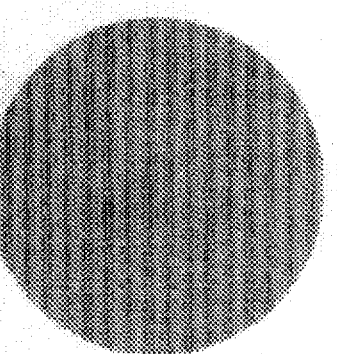
Fig. 23C          Fig. 23F          Fig. 23I

METHOD AND APPARATUS FOR PERFORMING AUTOMATED VISION PERFORMANCE TESTS

TECHNICAL FIELD

This is a non-provisional application based upon an earlier filed provisional application Ser. No. 60/004,595, filed Sep. 27, 1995.

The present invention relates generally to medical diagnosis instruments for testing visual functions in the human eye, and is particularly directed to testing the performance sensitivity of the contrast characteristics of a human eye. The invention is specifically disclosed as a diagnostic test that can be performed automatically by use of a computer using computer-generated graphic displays that are presented to a human patient, and by measuring the responses of the patient to various visual stimuli. Different grades of visual sharpness, such as sharpness detection, sharpness resolution, and contrast sensibility, are measured at the human eye.

BACKGROUND OF THE INVENTION

The existence of physiologic values in the function of some organs or systems of the human body, for example: blood pressure, auditive capabilities or, in the case of human eye, the different grades of myopia, and other symptoms have been useful in the prior art with respect to medical (or ophthalmological) diagnostic instruments. Those values—or the way to measure them—once known have become standards for the scientific community. In all cases it is now accepted that a minimal variation gap is considered as being normal, or (in other words) as "physiologic variations" which are different than "pathologic variations". Pathologic variations are ones that do not fit in the normality gap, based upon statistical samples.

SUMMARY OF THE INVENTION

Accordingly, it is a primary object of the present invention to provide a visual performance testing system which improves the precision and automatic data gathering of human patient test data by use of a new method of visual performance metering of the human eye, for the purpose of more accurate ophthalmologic diagnosis.

Additional objects, advantages and other novel features of the invention will be set forth in part in the description that follows and in part will become apparent to those skilled in the art upon examination of the following or may be learned with the practice of the invention.

To achieve the foregoing and other objects, and in accordance with one aspect of the present invention, an improved visual performance tester is provided, sometimes referred to as a "VPT" ("Visual Performance Tester"), which presents to the ophthalmologist not only very precise information, superior to conventional systems available worldwide, but tests vision sensitivity by use of contrasting images. One of the main features of this invention relates to the advantages provided by a "cutting edge technology" to generate software-controlled images on a personal computer's or workstation's monitor screen that provides contrast images on the monitor screen under a controlled-lighting environment. In addition, multimedia-type display presentations can allow an interactive participation by the patient, even those hearing impaired. Furthermore, an important aspect of the present invention is the ability to measure the time it takes for the patient (test subject) to give the answers required by the test, adding a new dimension to the visual tests.

The visual performance tester of the present invention surpasses the limits of the normal testing range by use of the embodiment disclosed hereinbelow, and will allow a physician to detect at early stages a wide spectrum of pathologies of human vision. The information provided by the tester of the present invention informs the physician when a patient's visual performance test yields a result below the medium (determined by statistics) of the pertinent spatial frequency. Spatial frequency is defined as the size of an image the eye is able to see.

What is known in ophthalmology as the Snellen chart (which consists of black images over a white background) is used to help determine a patient's visual sharpness. After the original Snellen chart was developed (in 1862), some scientists, based on Shade's work (in 1955) established the theoretical basis for the measuring the contrast sensibility function in the human visual system to improve the analysis, by use of gray sinusoidal bands instead of the letters used by Snellen. Factors that modify the sensibility of contrast are the background illumination, size of stimulus, temporal characteristics, orientation (and other characteristics). The theories behind the sinusoidal bands were used as a basis for the development of the present invention's visual performance tester.

Using customized software, the visual performance tester of the present invention has the mathematical capability to randomly generate images of bands inside a circle on the screen on a computer monitor. The patient establishes the speed of the process by answering questions posed by the personal computer (PC) system provided with the visual performance tester in such a way that the patient's visual sensitivity is intelligently evaluated. The patient's delay (or lack of delay) in providing answers is used in this evaluation by the present visual performance tester, which determines what image should be placed next upon the monitor screen by analyzing the input provided by the patient. Any mistakes made by the tester's operator and/or those made by the patient (which would otherwise introduce bias) are minimized by the PC system provided with the visual performance tester.

Many advantages are realized by using the automatic procedures of the present invention: [1] procedures and conditions are normalized in order to better compare one test result to another; [2] results can automatically be compared with other test results using a database containing previous test results for the same patient, or results from other persons who previously have been tested; [3] patient's or operator's psychological factors (e.g., if the patient is tired, or under stress) are taken in account and are minimized in the final results. The information gathered by the physician using the present visual performance tester is similar to information that can be collected by current clinical procedures of contrast vision testing. However, the results obtained by the present visual performance tester during the experimental testing are superior in accuracy, range of parameters measured and evaluated automatically, and precision, which allows the ophthalmologist to expect acquisition of quite precise, easily obtainable information that is comparable to the data obtained by other testing methods on patients, but with superior results.

The present visual performance tester can be programmed to operate with several languages (even native ones). A prototype has already successfully demonstrated its capabilities to operate in English, Italian, Portuguese, French, German, Spanish or Quechua (native language). In addition, the prototype can be used with Windows and OS/2 operating systems as computer system platforms. Furthermore, a large number of ophthalmologists may desire to store information acquired by the present visual performance tester in a single database, and network connectivity can be used to communicate data from many such PC testing systems to a single network server. The standard of vision normality for contrast sensitivity will likely evolve in both precision and universality as a result of a larger amount of cases recorded by use of the present visual performance tester.

Another feature of the present visual performance tester is the use of a new statistic that may emerge as a new standard in the visual performance metering of human patients. The new statistic is a mathematical quantity, and is referred to herein as a visual balance test, or "VPT Balance," which is a number, in decibels, that represents a patient's vision performance as compared to a database of previously tested patients. Using the database information, a statistical mean of contrast thresholds (in dB) is calculated at each of various spatial frequencies, the current patient's test results (also in dB) are compared to that mean at each of those same various spatial frequencies, and the deviations (in dB) at these spatial frequencies are accumulated to provide a single numeric result that gives a reliable "quick" indication of this patient's vision performance.

Still other objects of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

FIGS. 23A–23I illustrate various circles with bands having different sizes and contrasts, as used in the visual performance tester of FIG. 1.

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

Figure 1:
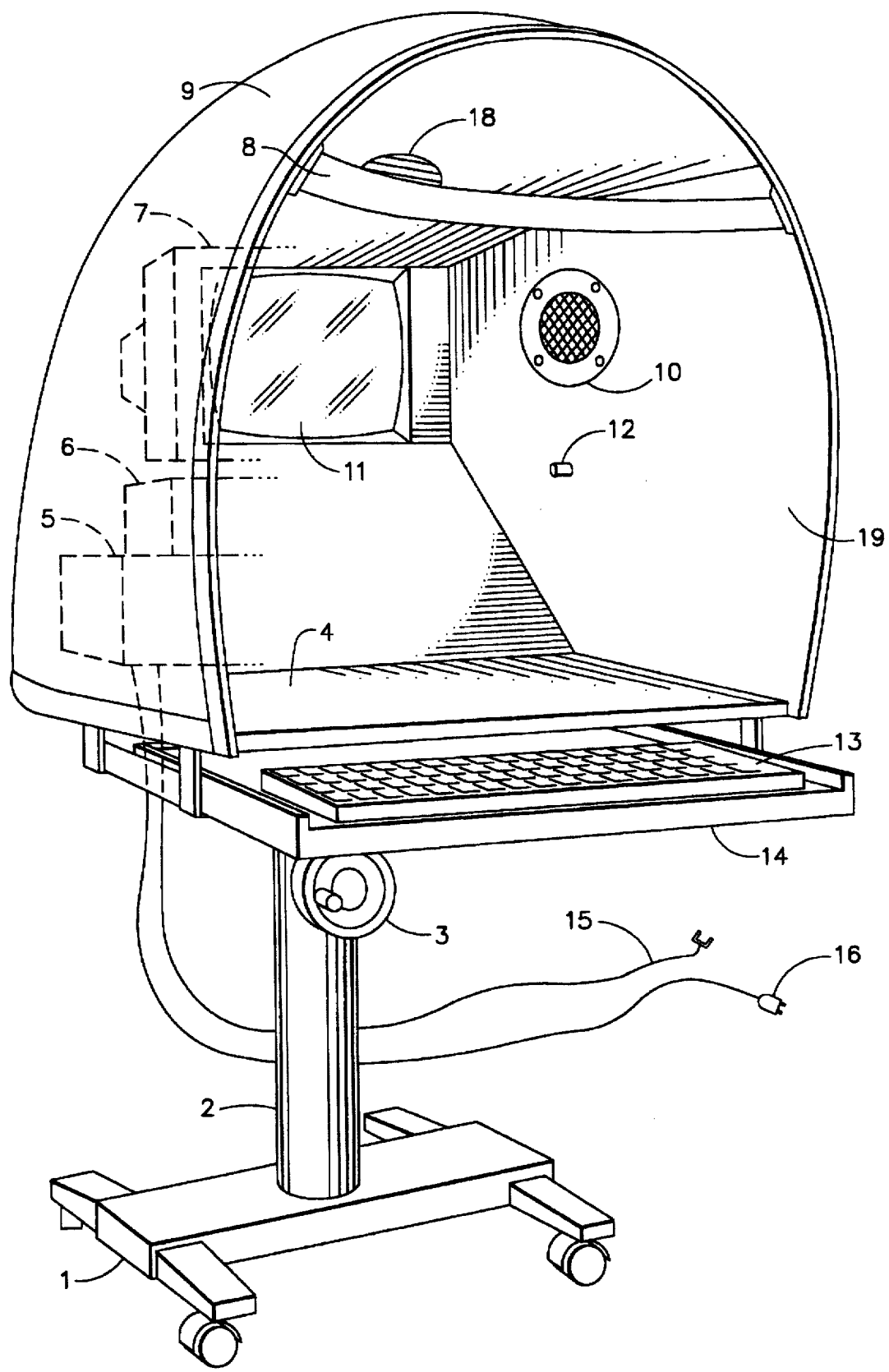
FIG. 1 is a front and side perspective of a visual performance tester constructed according to the principles of the present invention, showing the dome with associated electronic hardware, including a personal computer and monitor, audio amplifier and speaker, and communications line, and also showing the head support and the adjustable working desk.
Figure 2:
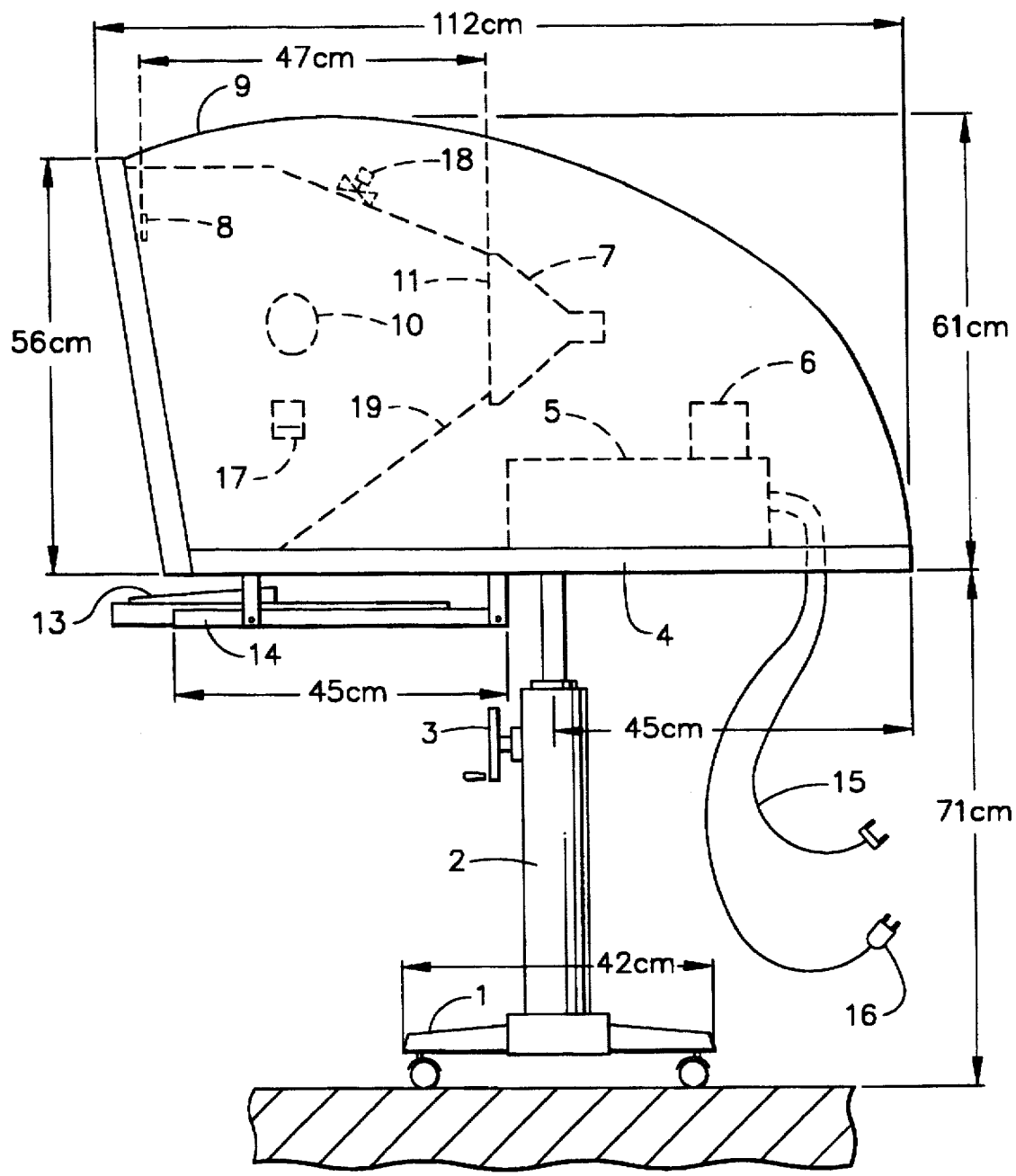
FIG. 2 is a side elevational view of the visual performance tester of FIG. 1, in which some of the more important dimensions are given, expressed in centimeters.
Figure 3:
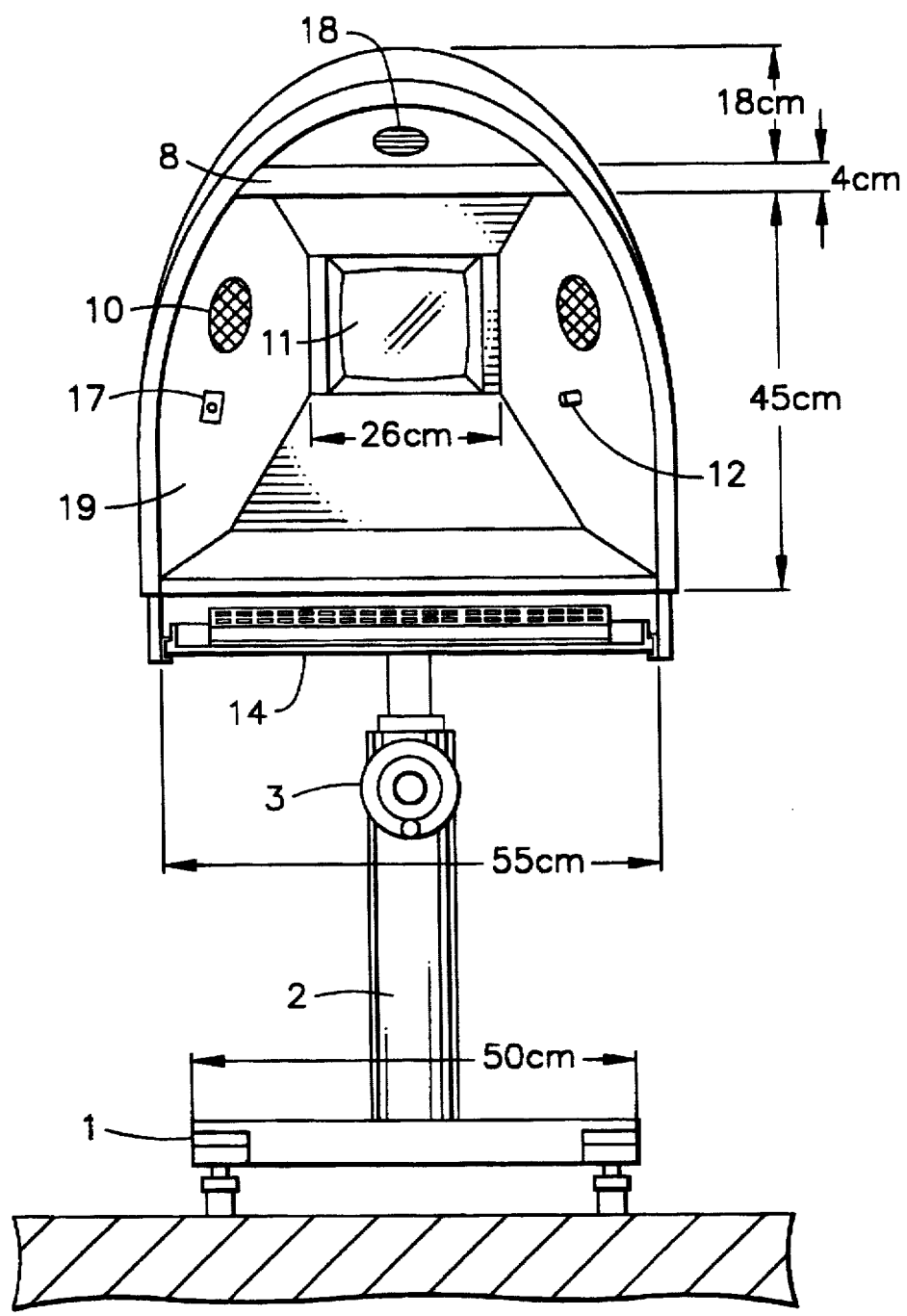
FIG. 3 is a front elevational view of the visual performance tester of FIG. 1, in which some of the more important dimensions are given, expressed in centimeters.
Figure 24:
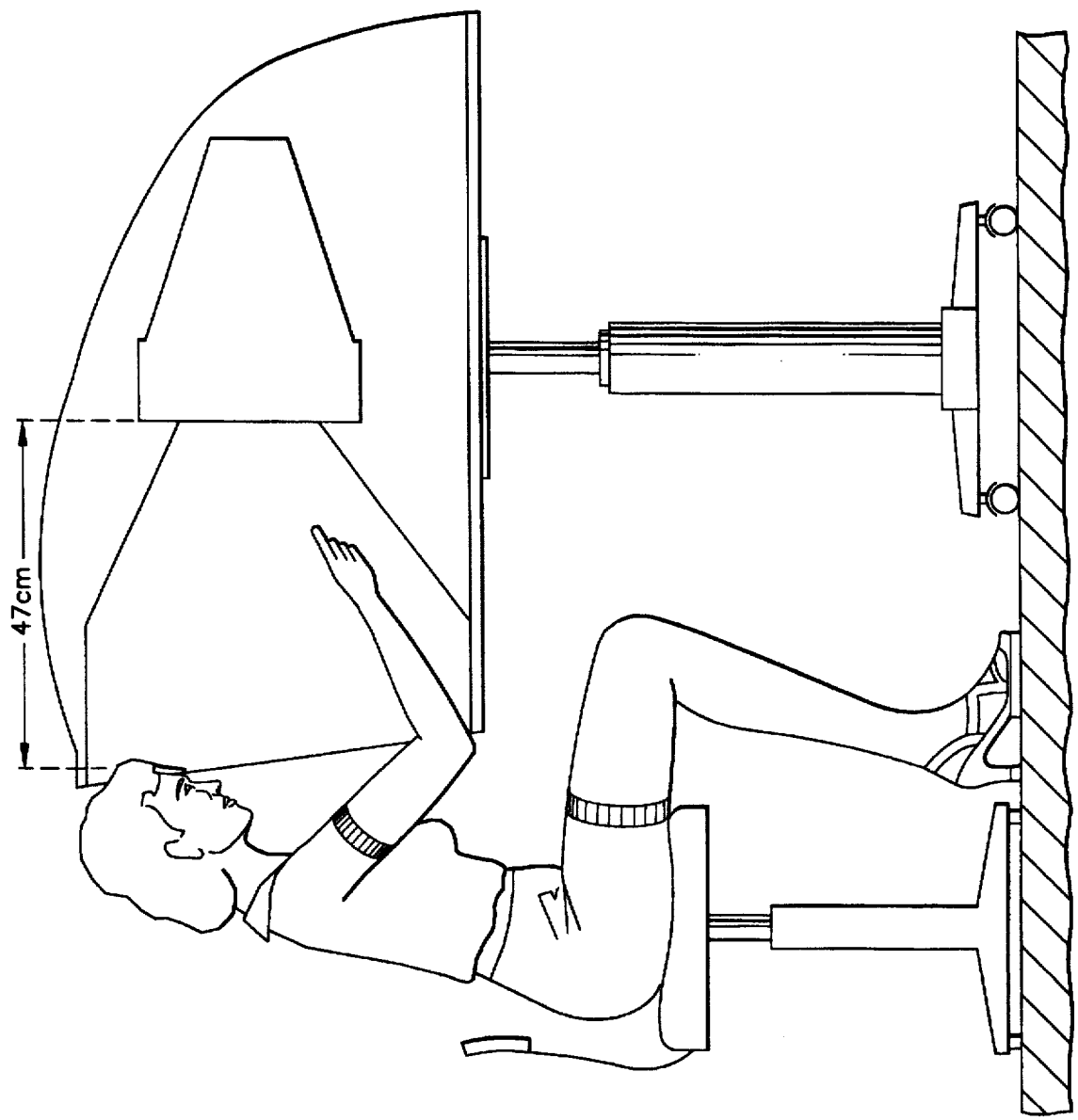
FIG. 24 is a diagrammatic side view showing a patient in the correct position (inside the dome) for undergoing the visual performance test of the present invention.
Figure 25:
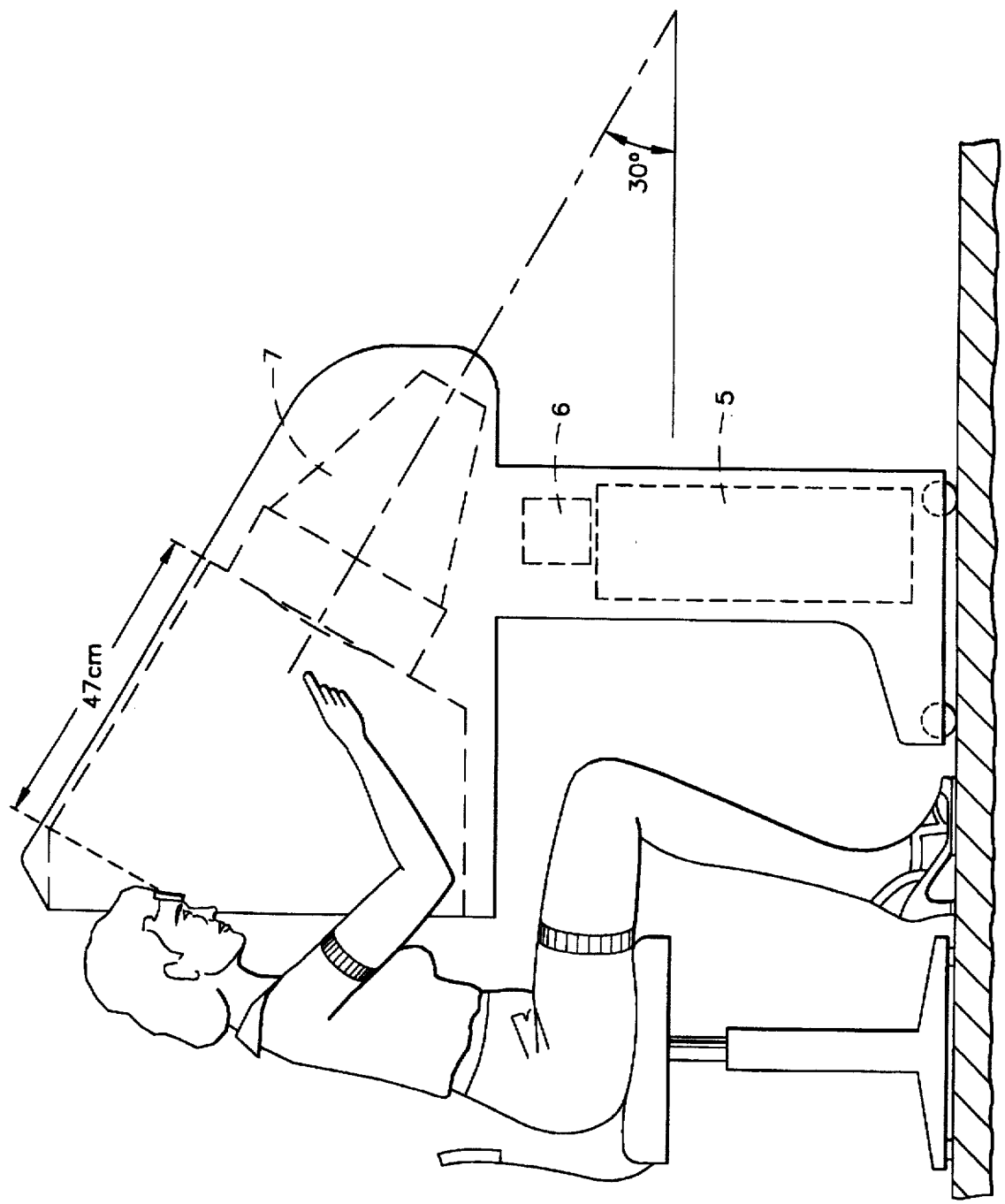
FIG. 25 is a diagrammatic side view showing a patient in the correct position (inside the dome) while using an "ergonomic model" of the visual performance tester, while undergoing the visual performance test of the present invention.

Referring now to the drawings, FIG. 1 shows a from and side perspective view of the present visual performance tester. FIGS. 2 and 3 provide elevational views from the side and front, respectively, of the visual performance tester of FIG. 1, and certain preferred dimensions are given. FIG. 24 further provides a side diagrammatic view of the visual performance tester of FIG. 1, along with the position that the patient should assume during a test session.

The head of the patient is inserted in the dome 9 of the visual performance tester, and dome 9 is designed to reduce the lateral vision of the patient, and to reduce external illumination, while allowing the patient to adjust the visual angle of the monitor 7, as needed. Scientific criteria requires experiments and studies to be carried out under equivalent conditions. Because of the visual sharpness is dependant of the lighting conditions of the environment and the distance between the patient's eye and the screen, the values for distance and brightness are constrained to remain constant in every test.

The design of the dome 9 plays an important role to guarantee the precision of the test results, and allows for a much more accurate comparative analysis. Its configuration allows the amount of light that the eye receives to be precisely controlled in every test. The dome's interior surface, generally depicted at index numeral 19, preferably is of a non-reflective nature (such as a color of flat black) and is opaque.

The distance between the monitor's screen and patient's eye is fixed by use of a supporting device 8 attached to the dome where the patient locates his forehead, thereby avoiding changes or variations in the test results due to variations in this distance. The preferred distance has been determined through a mathematical calculation establishing the optimal distance for the purpose of the test. This preferred distance between the patient's eye and the screen is 470 mm when using a 15-inch monitor having a resolution of 1280×1024 (or higher) pixels, where the pixel horizontal size is 0.19 mm or less.

The position of the patient in the dome provides for ease in listening to the audio instructions of the tutorial and test software by providing speakers 10 of close proximity. The audio volume could also be regulated with a volume control 12 that is adjustable by the hands of the patient. An audio amplifier 6 provides a sufficiently strong outgoing audio signal from the computer system 5, thereby maintaining a high sound quality.

The testing process is controlled by a personal computer or workstation, generally designated by the index numeral 5. The apparatus includes a power switch 17 that provides energy to the entire system. The present visual performance tester can operate with an AC power source and contemplates the use of different voltages according to the country of installation (using either 220 VAC or 110 VAC), and connected via a power cable 16. A telephone line 15 is typically provided to the present visual performance tester, thereby allowing local or long distance connectivity to a network.

Specially-designed graphics can be displayed on the monitor screen 11, including "touchscreen" capabilities in order to simplify the way in which the patient will deliver the answers (see FIGS. 16 and 17), for an example of use of various screen areas. A fan 18 is preferably installed inside dome 9 to prevent overheating of the microprocessor and other electronic components by maintaining air circulation inside the dome. During the execution of a test, the computer's keyboard is hidden under a table 4, and access to the keyboard 13 is provided by a sliding keyboard support 14.

The dome 9 preferably is mechanically and visually attached to table 4, and the entire structure is provided with wheels 1 (for portability) and a height-adjustment wheel 3 that controls the distance that a leg 2 extends, to assure that no variation (other than the subject examined) will alter the result of the test. The patient is preferably seated in a comfortable chair with wheels and adjustable height (see FIG. 24).

Initialization & Configuration

Figure 4:
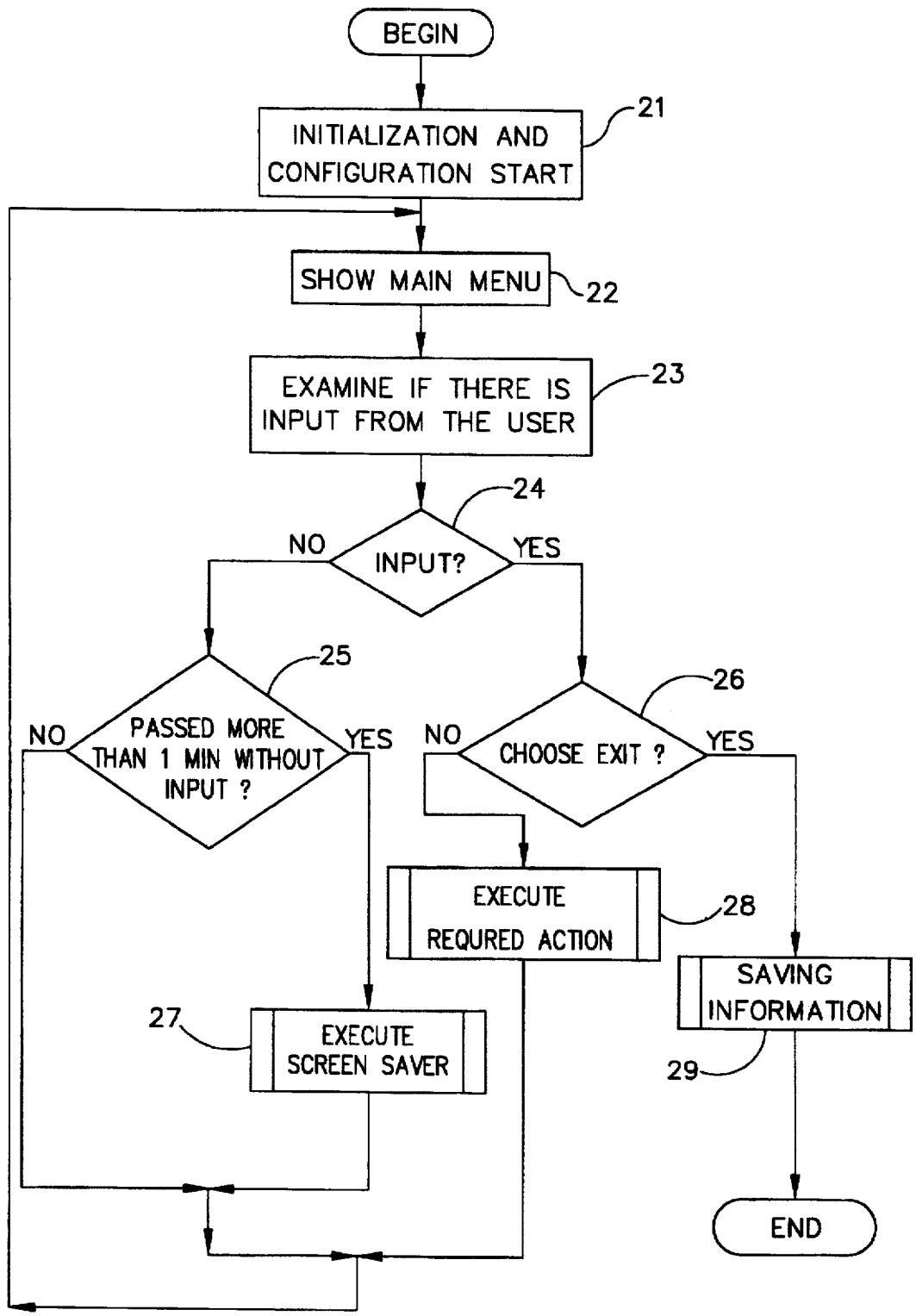
FIG. 4 is a flow chart of the general process control steps of the "core module" that control the automated functions of the visual performance tester of FIG. 1. The blocks depicted in "double line" rectangles identify subprograms described more completely on other, separate flow charts herein.

Once the visual performance tester of the present invention is turned on, the provided software starts execution. The major process steps are diagrammed in FIG. 4, and certain of the function blocks of the flow chart (i.e., the blocks in "double" vertical lines) are described in greater detail on other figures. For example, the initialization function block 21 is depicted in further detail on FIG. 5.

Figure 5:
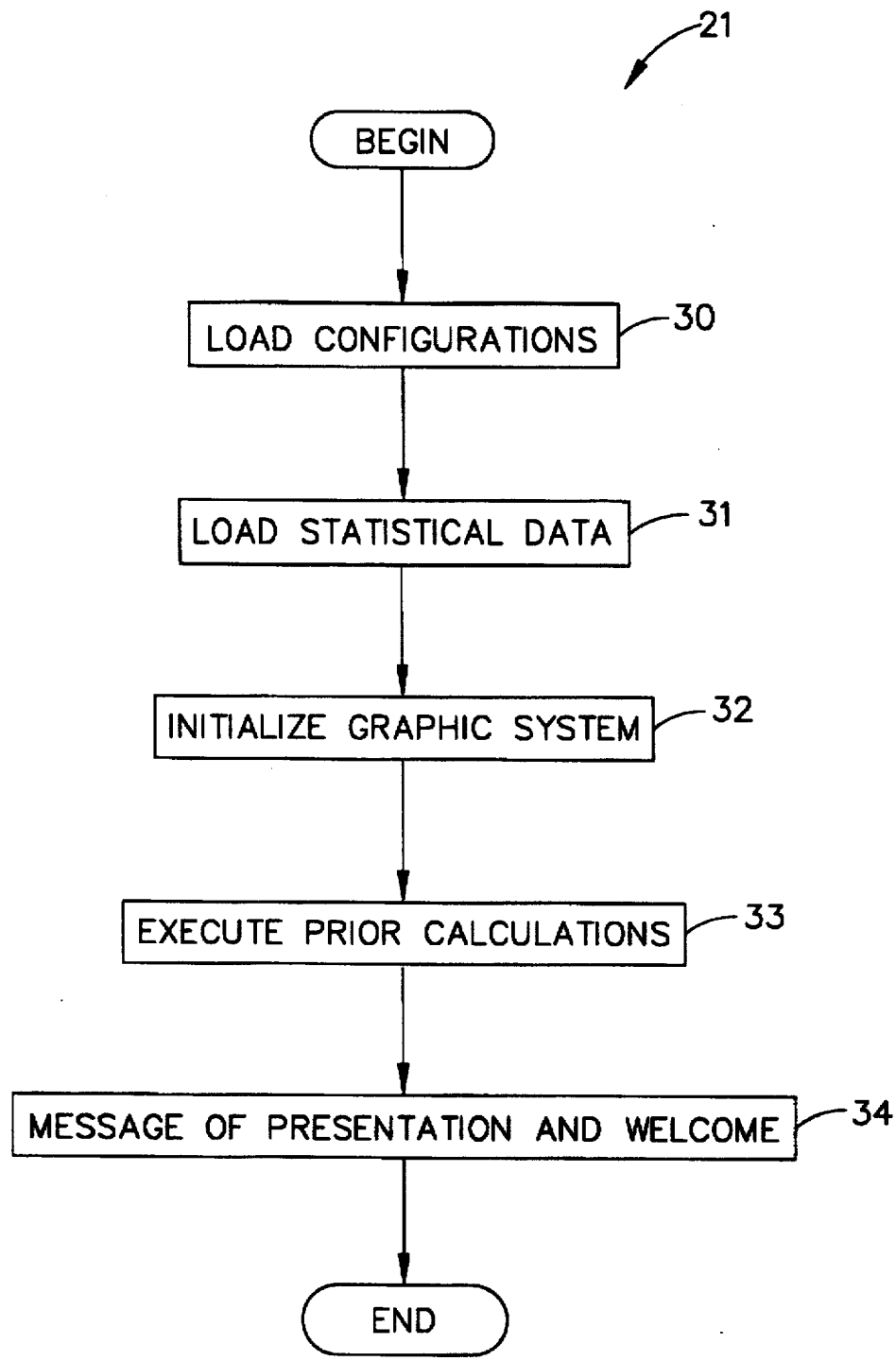
FIG. 5 is a flow chart showing the process of initialization of the visual performance tester of FIG. 1.

The first step that the software executes is the initialization procedure function block 30, which configures the system (see FIG. 5). Function block 30 loads into memory the last configuration used, or the one chosen as the default. In addition, a system operator is able to select from a set of options, before running a new test. The set of options allows the operator to choose from a number of different languages and screen formats. The different languages option is patient-oriented, rather than physician-oriented, and the patient may immediately select the language of his own idiom.

All pertinent statistical and updated data are loaded at function block 31, and the initialization of the graphics system for the correct operation of the video displays occurs at function block 32. Function block 33 carries out a set of previous calculations in order to provide a faster and more reliable test. The starting process ends with a welcome message (to be displayed to the patient under test) at function block 34.

II. Main Menu

Figure 6:
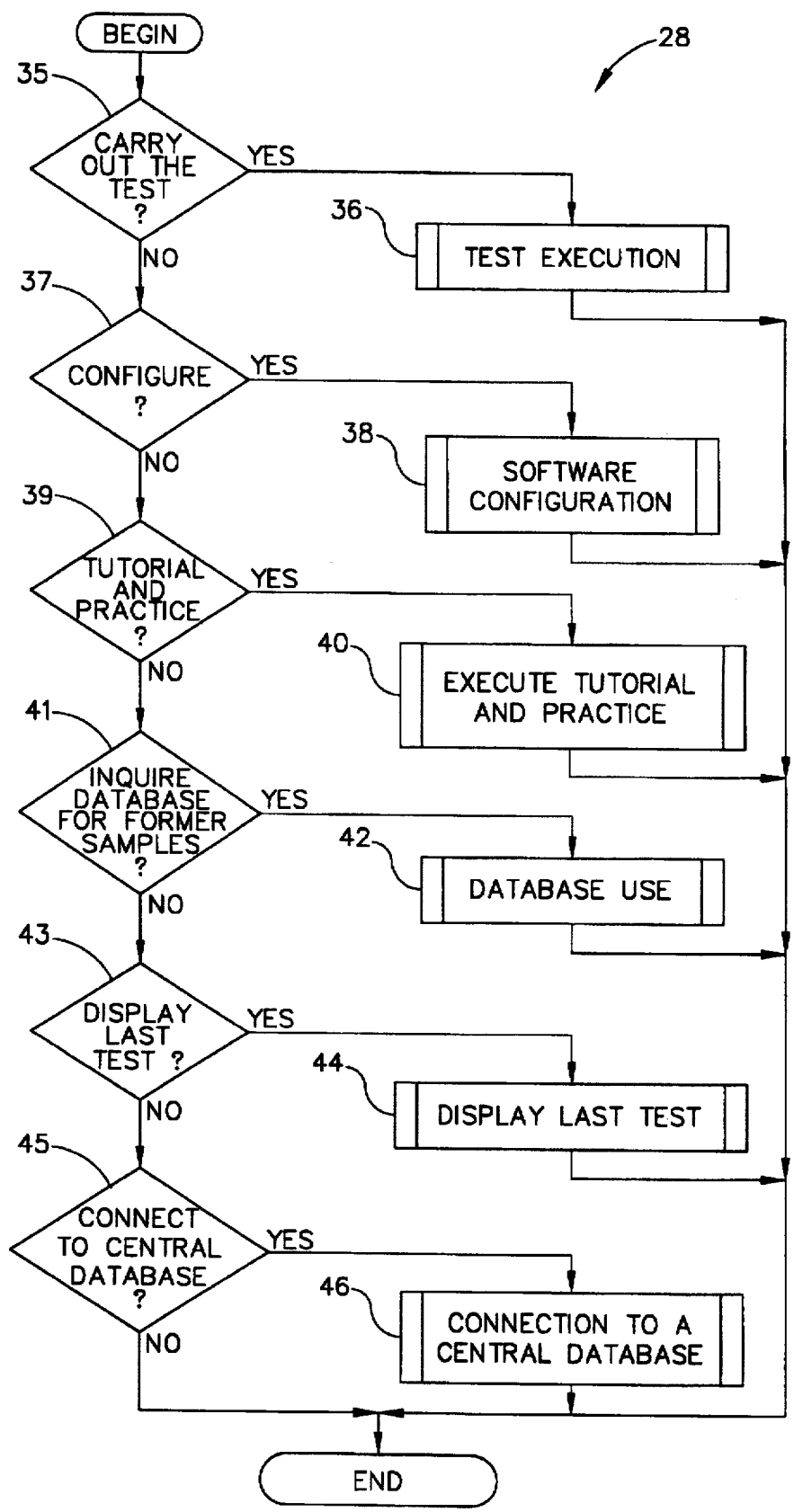
FIG. 6 is a flow chart that shows the method that the operator's orders are processed by the visual performance tester of FIG. 1.

After showing the introductory screen, the main menu of the program is displayed, under the control of function block 22. All inputs provided by the system operator while using the main menu, except the exit option, are processed later by function block 28. The exit option is processed later by decision block 26 and function block 29. The main menu allows the operator to select from a number of different functions (see FIG. 6), including: [1] run a test session (see decision block 35); [2] configure the default information considered suitable for the patient and select the screen format (see decision block 37); [3] run tutorial and test practice routines (see decision block 39); [4] inquire about former samples (see decision block 41); [5] display the results of former tests (see decision block 43); and [6] optionally connect to a central database (see decision block 45). For every option selected by the system operator, the software executes the appropriated actions as described in function blocks 36, 38, 40, 42, 44, and/or 46 (which are each described in greater detail hereinbelow).

Later Steps

The system, under control of the software at function block 23 and decision block 24 (see FIG. 4), waits for the operator to select one or more of the available options. When a selection is made, a new set of options is opened, as described at the bottom of FIG. 4. If no instruction is selected for a time period (such as one minute), as determined by decision block 25, a screen saver executes at function block 27 to protect the monitor. If the patient makes an entry, the "exit" option (decision block 26 is displayed, which allows the operator or patient either to exit or not, thereby either directing the logic flow back to the main menu screen at function block 28, or to save data at function block 29, where the information is stored to be ready for the next test and the program ends.

Screen Saver Execution

Figure 7:
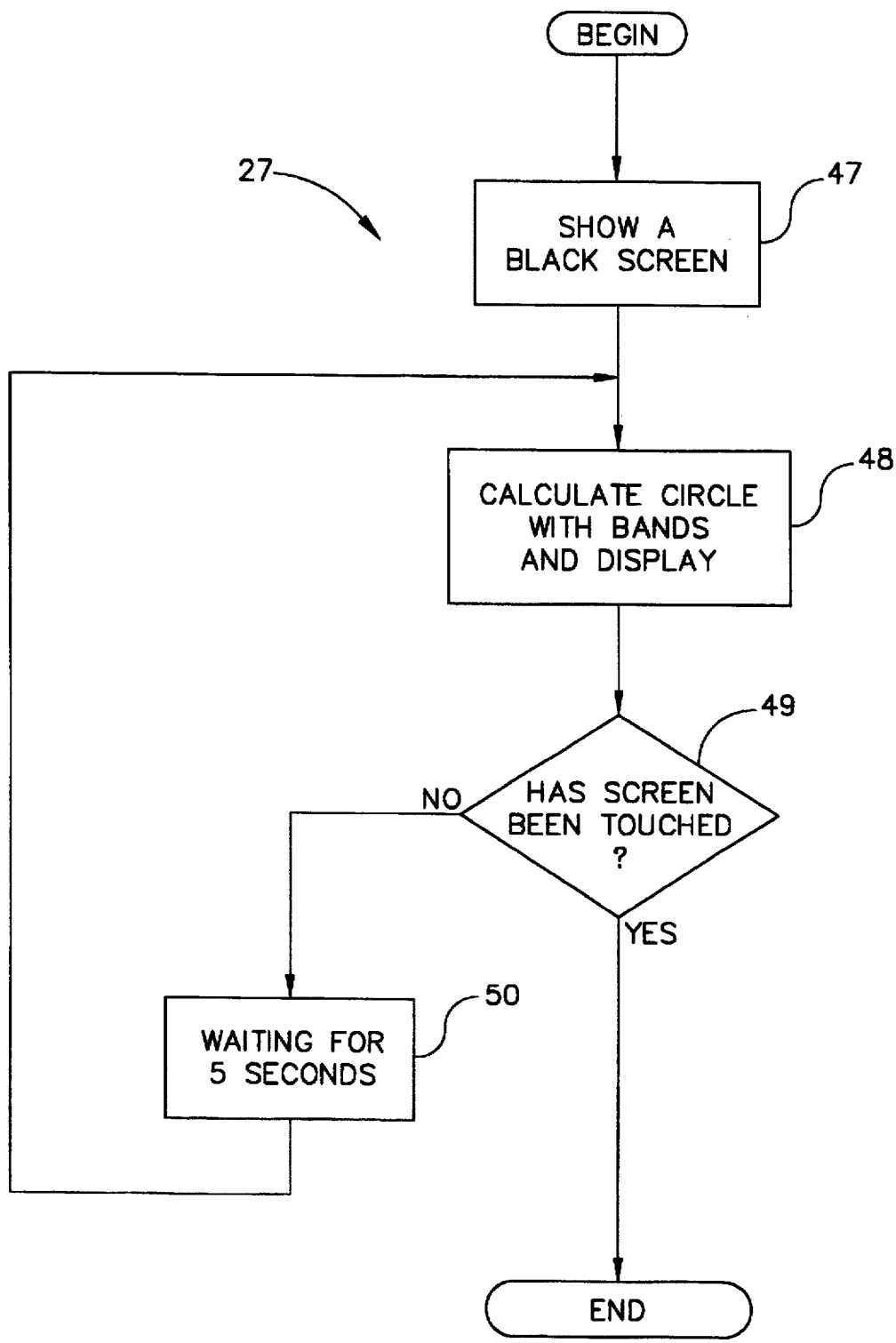
FIG. 7 is a flow chart describing the execution of the screen saver of the visual performance tester of FIG. 1.

The logical steps to perform the execution of the screen saver is provided on FIG. 7. The monitor screen is first configured using a black screen as a background at function block 47, then a circle with interior parallel bands in gray tonalities is displayed at various locations according to function block 48. Decision block 49 determines whether or not the patient touches the screen. After waiting for a pre-determined time duration, such as five seconds (see function block 50), if the answer is NO, then function block 48 displays another circle at a new screen location. If the patient has touched the screen, then the logic flow proceeds to function block 22 (on FIG. 4), and displays the main menu (e.g., for the next patient to be tested).

Saving Information

Figure 8:
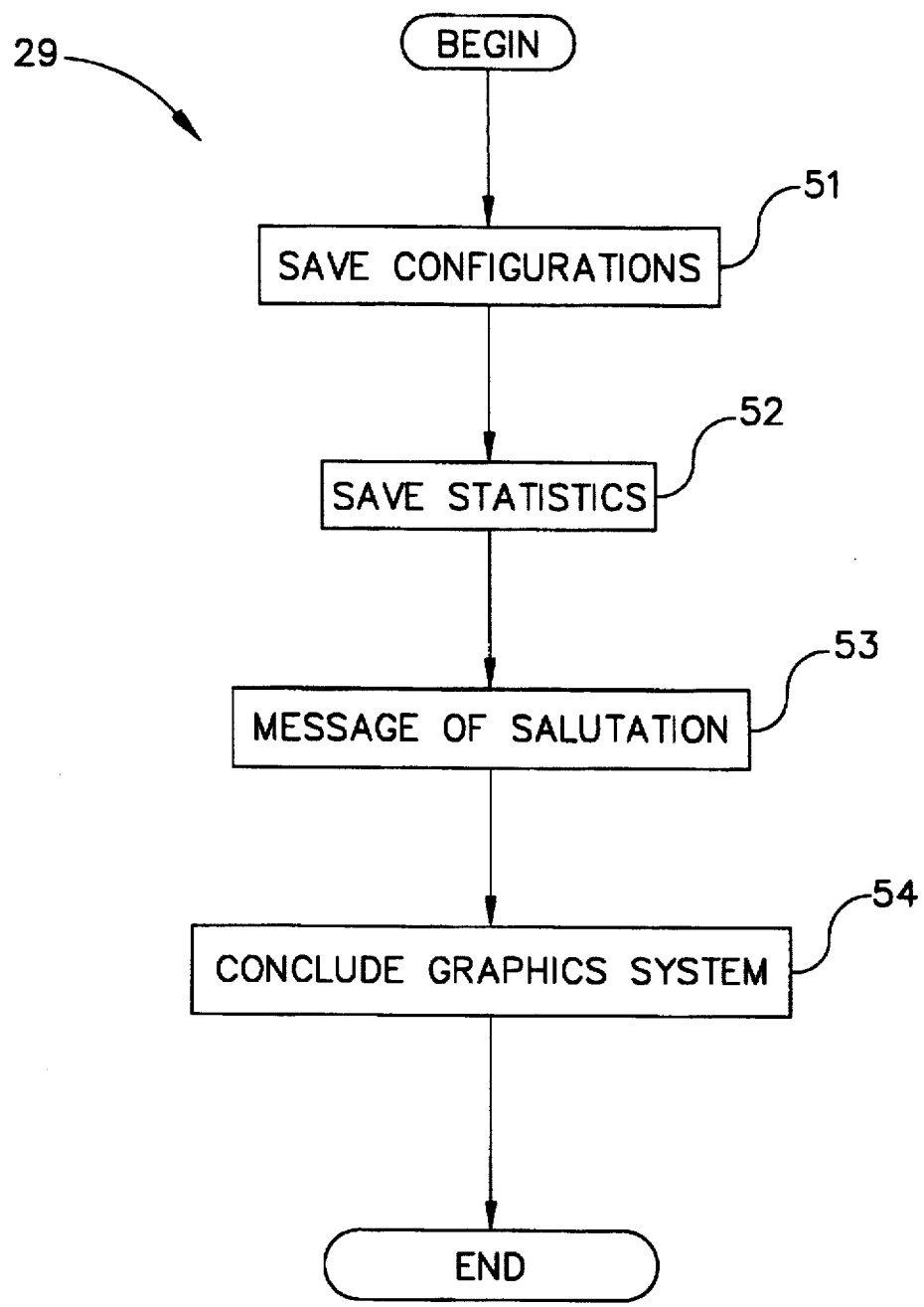
FIG. 8 is a flow chart showing the procedure for saving important information and data after a test session of a patient to be implemented before the visual performance tester of FIG. 1 is de-energized.

Before exiting the test procedure, the software always saves the information acquired in the most recent test, as shown in FIG. 8. Function block 51 saves the protocol and configuration used, and stores the new information in the form of updated statistics at function block 52. A salutation message indicates (to the patient) that the test has concluded at function block 53, and the graphic display operations terminate at function block 54.

Test Execution

Figure 9:
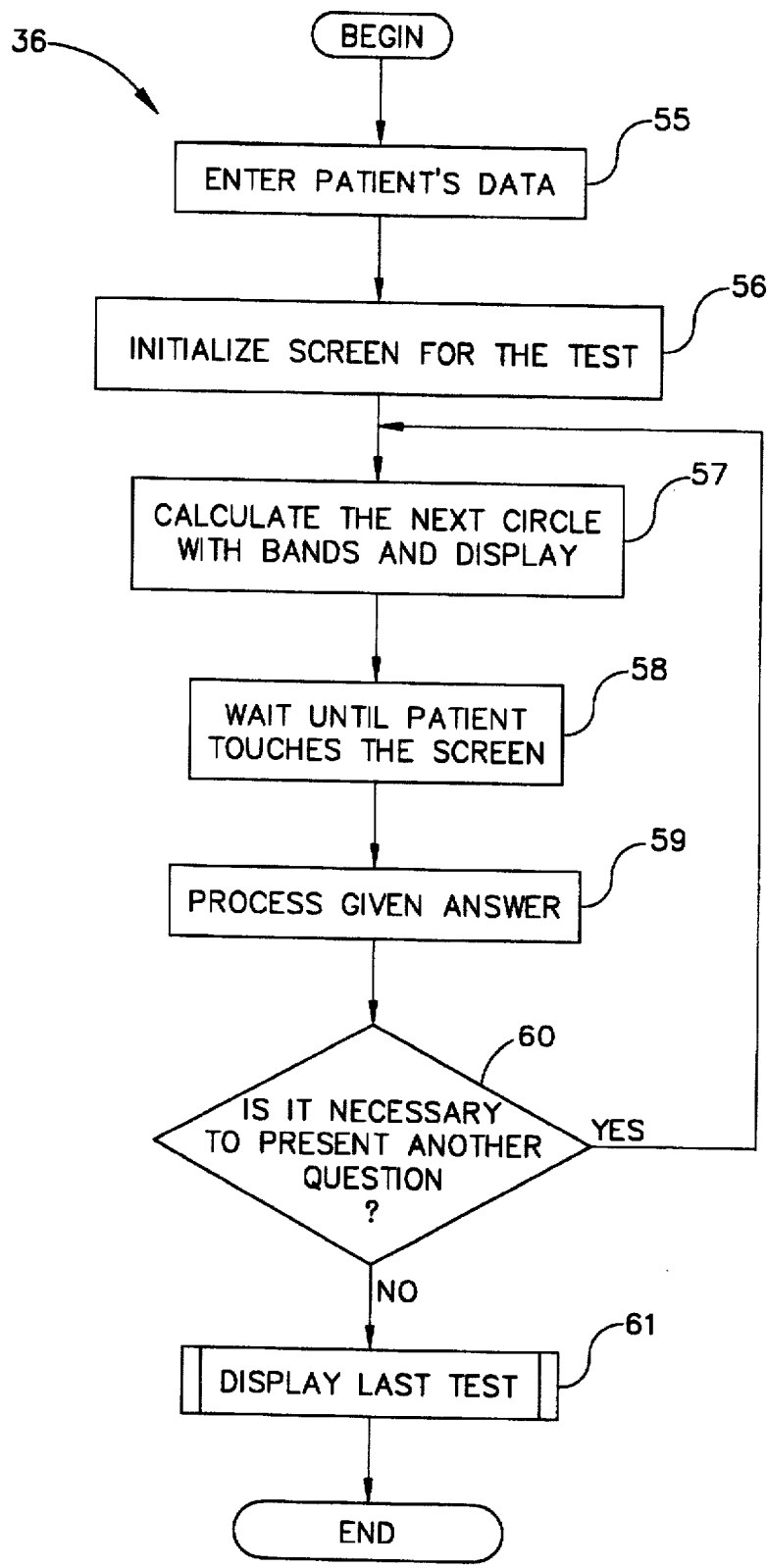
FIG. 9 is a flow chart showing the procedure by which the visual performance tester of FIG. 1 executes a test session with a human patient.
Figure 22:
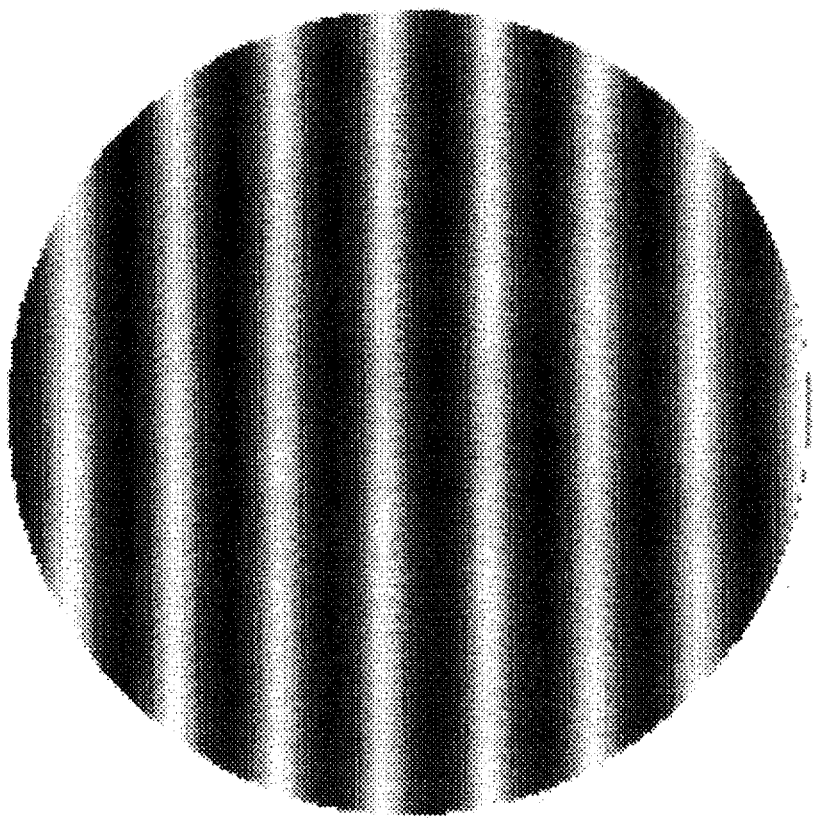
FIG. 22 is a detailed illustration of a circle with vertical bands, which is used in the visual performance tester of FIG. 1.

To execute a visual performance test of a patient (see FIG. 9), the system operator (or the patient) must first enter the patient's pertinent data at function block 55. The screen is then initialized at function block 56 for the new test now beginning. Using the computer's multimedia audio capability, the system directs pertinent questions to the patient until the computer determines that no more questions need be asked at this time (at decision block 60). During the question/answer session, and according to the different answers provided by the patient at function blocks 58 and 59, if more information is needed, the logical flow will be directed to function block 57 where circles in the center of the screen will be displayed having an interior set of bands and having multiple configurations (i.e., having different band attributes such as color, width, number, position) being displayed one by one, and at various locations on the screen 12 (see locations 116 and 121 on FIGS. 16 and 17, respectively, and see FIGS. 22 and 23).

When the patient sees the bands and their (angular) inclination, he or she is supposed to touch the screen at a particular location as a feedback answer. If nothing is perceived by the patient, a location near the bottom of the screen should be touched, as, for example, at locations 117, 122 or 127 on FIGS. 16 and 17, respectively. If the bands of the displayed circle are inclined toward the left, the patient should touch the zones numbered 113, 118 or 124 on FIGS. 16 and 17, respectively. If the bands of the shown circle are vertical, he/she should touch the zones numbered 114, 119 or 125 on FIGS. 16 and 17, respectively. If the bands of the circle are inclined toward the right, he/she should touch the zones numbered 115, 120 or 126 on FIGS. 16 and 17. The button situated in the area 123 serves to cancel the test, if touched.

For every answer entered by the patient, the software assigns an adjusted waiting time, after which a new circle is displayed by function block 57. According to the time delay by the patient before providing his/her answer (at function block 58), a mathematical calculation is performed at function block 59 which determines which image is next going to be placed on the screen. The test advances until the decision as to whether or not any further questions need be asked of this patient is made at decision block 60.

There are twelve (12) different possible sizes of bands in the preferred embodiment (in which the size is related to the band's spatial frequency) and more than 4000 different contrasts for every size of band. For every size of band (i.e., its spatial frequency), the visual performance tester of the present invention will search for the minimum contrast the patient can perceive. The first circle shown is determined mathematically from previous tests made to other patients. The inclination of the bands are randomly generated (see FIG. 23), however, the illustrated embodiment limits the inclination angles to three possible choices to make it quicker and easier for the patient to answer the visual performance tester every time a new circle with bands is displayed. Because of the random selection of the inclination angle, the patient will not be able to determine in advance the inclination of the bands of the next circle to be displayed.

FIGS. 23A–23I are examples of the actual test images that a patient will view when using the visual performance tester of the present invention. At one level of testing, for example, the visual performance tester is attempting to determine the minimum contrast the patient can see by displaying different band sizes, as shown in FIGS. 23A–23I. If the band size of FIG. 23A is the first circle shown and the inclination is correctly answered by the patient, then the contrast will be reduced, and the next circle will be much like the one shown in FIG. 23B. In the preferred embodiment, the inclination of the bands will never be the same from one circle to the immediate next circle. If the inclination is once again correctly answered by the patient, then the contrast will be reduced again, and the next circle shown will be much like the one shown in FIG. 23C.

When the patient is not able to see the bands inside one of the circles, then the contrast of the previous circle is the "threshold" (i.e., the minimum contrast the patient can perceive) for the spatial frequency (i.e., band size) currently being tested. At this point, the visual performance tester can automatically show a new circle having an increased contrast to refine the patient's threshold determination once the patient responds either with the incorrect answer, or no answer at all within the time limit.

Figure 13:
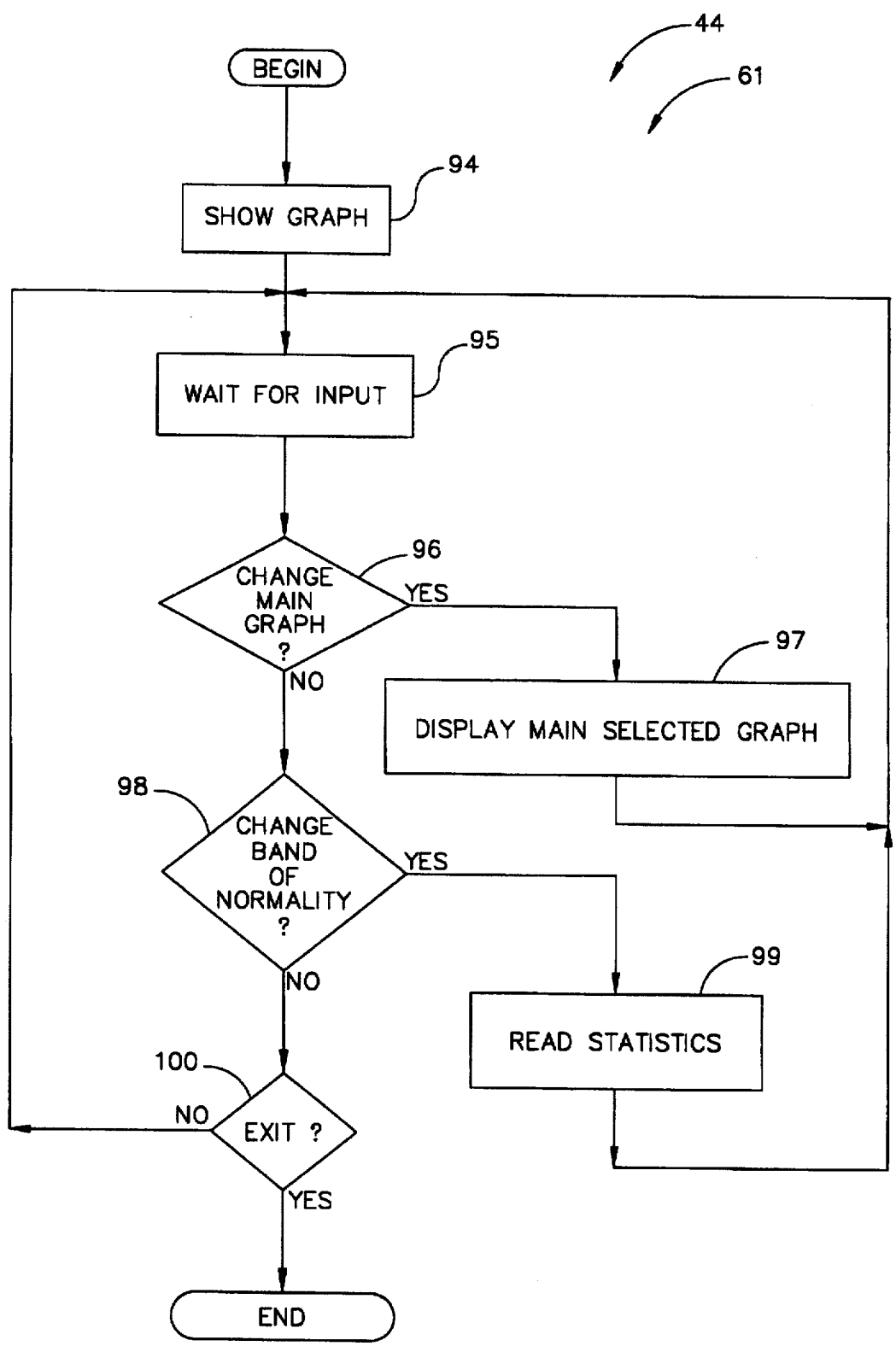
FIG. 13 is a flow chart that illustrates the steps performed by the visual performance tester of FIG. 1 to display a vision test on the monitor screen, as well as options that are available for making changes to the configuration of the visual performance tester of FIG. 1.

This procedure preferably is repeated for each of twelve (12) spatial frequencies for every patient. A normal test run will show about 100 circles to each patient. FIGS. 23D, 23E and 23F show another example of how the contrast is reduced for a different spatial frequency (size of band). FIGS. 23G, 23H, and 23I show a further example of this characteristic. As related above, the patient's threshold (minimum perceived contrast) will be determined at these different spatial frequencies. When the twelve (12) thresholds have been found, the results are displayed on the screen (see FIG. 13) by function block 61 on FIG. 9.

Software Configuration

Figure 10:
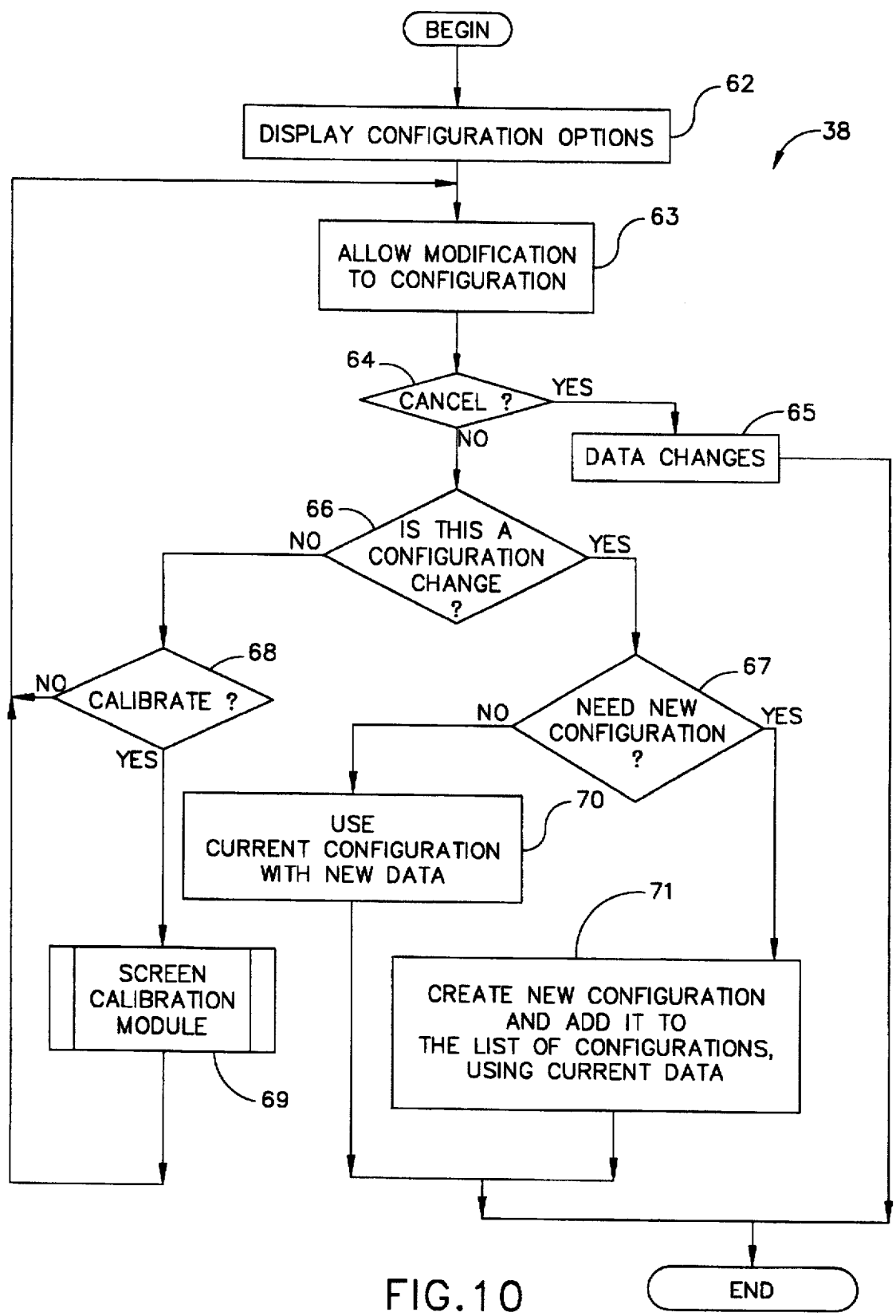
FIG. 10 is a flow chart showing the procedure for configuring the visual performance tester of FIG. 1.

During the step of configuring the software, the visual performance tester displays a screen with various options, at function block 62 (see FIG. 10). The operator can instruct changes to be made to this configuration at function block 63. After a configuration change is entered, if any, the "options" routine may be canceled at decision block 64, and if this occurs, the adjustments made will not be saved (at function block 65), and the former configuration continues to be in effect. When a new option is desired, decision block 66 decides whether or not a new configuration change is to be made, or if a calibration is to be performed. If a new configuration is to be made, decision block 67 determines whether a new configuration with the same data is to be created at function block 71, or whether the current configuration should be modified to be used with new data (at function block 70).

Figure 15:
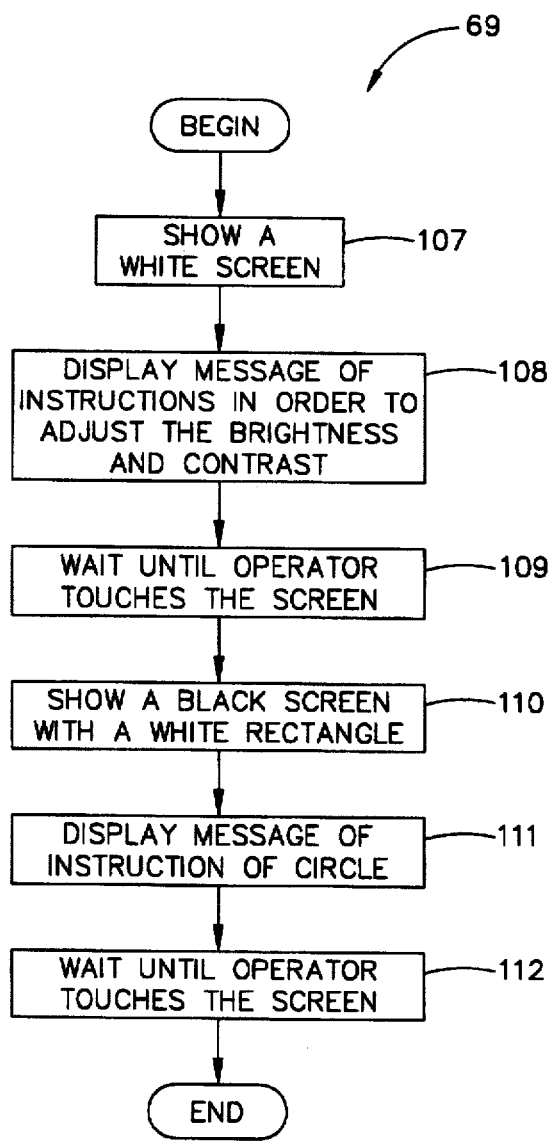
FIG. 15 is a flow chart illustrating the logical steps executed to perform a screen calibration operation by the visual performance tester of FIG. 1.

The screen configuration option at decision block 66 allows the visual performance tester to assess the brightness, contrast and size of the image in the monitor. Decision block 68 determines whether or not a calibration procedure has been requested. If the answer is YES, the software is supplied with a special application subprogram at function block 69 specially created to perform the calibration (see FIG. 15).

Execution of Tutorial and Practice Applications

Figure 11:
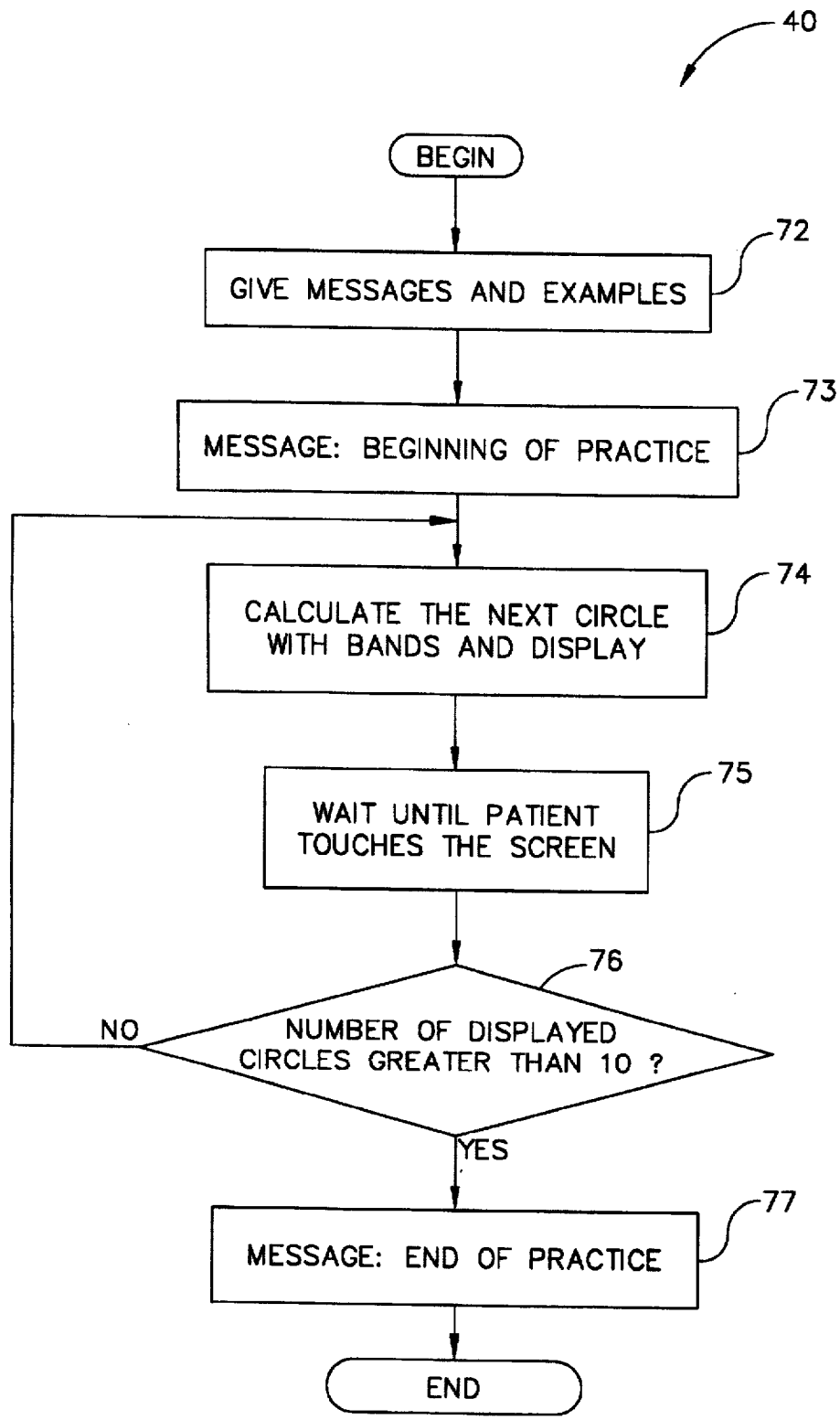
FIG. 11 is a flow chart showing the method for executing the tutorial and practice or "warm-up" exams provided by the visual performance tester of FIG. 1.

The vision tester includes a tutorial that shows the patient how to use the touchscreen answering system at function block 72 (see FIG. 11). After that is performed, a computer-controlled voice invites the patient to start a short practice run (at function block 73) to get him/her acquainted with the test procedure via a number of questions to adequately train the patient. The number of questions to train the patient is determined by decision block 76, and as a default value, is set equal to ten (10).

Figure 16:
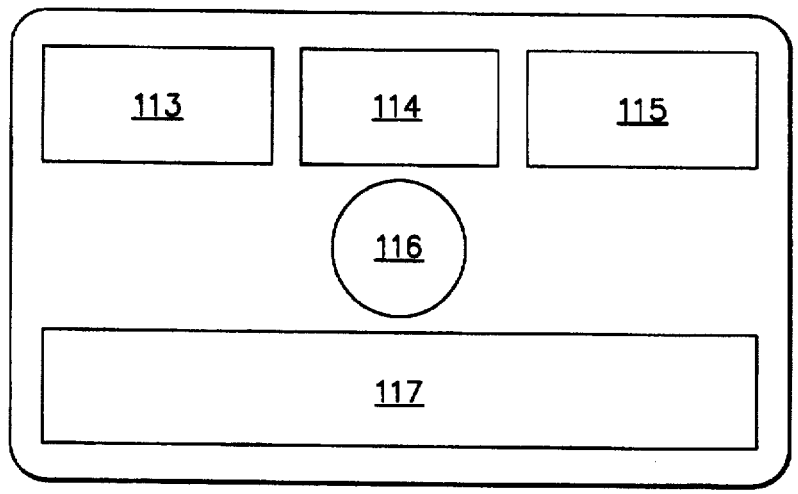
FIG. 16 is a diagrammatic view of a monitor screen displayed by the visual performance tester of FIG. 1, illustrating the division of the screen for touchscreen information input in a test mode in which no buttons appear upon the screen.
Figure 17:
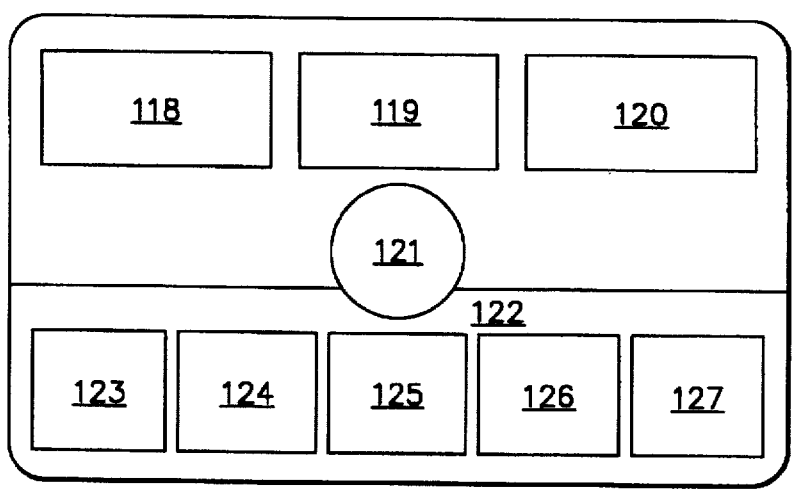
FIG. 17 is a diagrammatic view of a monitor screen displayed by the visual performance tester of FIG. 1, illustrating the division of the screen for touchscreen information input in a test mode in which buttons appear upon the screen.
Figure 18:
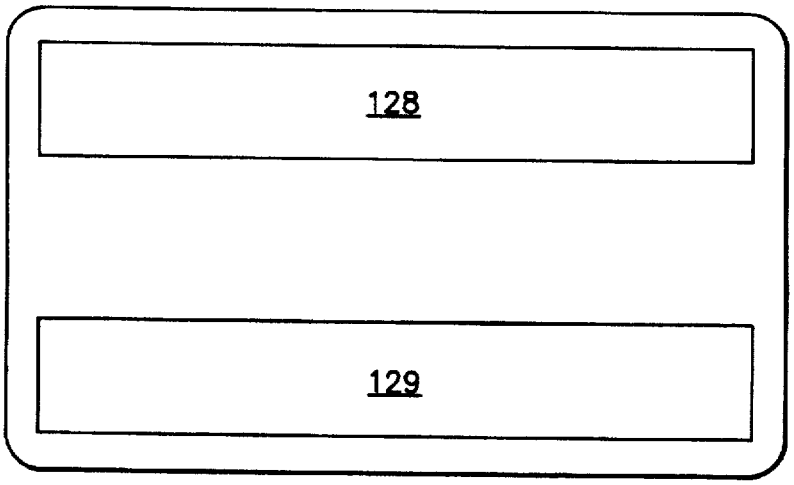
FIG. 18 is a diagrammatic view of a monitor screen of the visual performance tester of FIG. 1, illustrating the screen areas that are available to display written messages for hearing impaired patients.

Every question is accompanied by displaying one of the above-described circles with bands drawing, under the control of function block 74 (for examples of these circles, see locations 116 and 121 on FIGS. 16 and 17). As in a real test, the patient is expected to answer by touching the screen 12 at locations that indicate the patient knows the correct inclination of the bands (as detected by function block 75). After answering a number of questions (determined by decision block 76), a message on the monitor announces that the practice has finished, as controlled by function block 77.

Database Use

Figure 12:
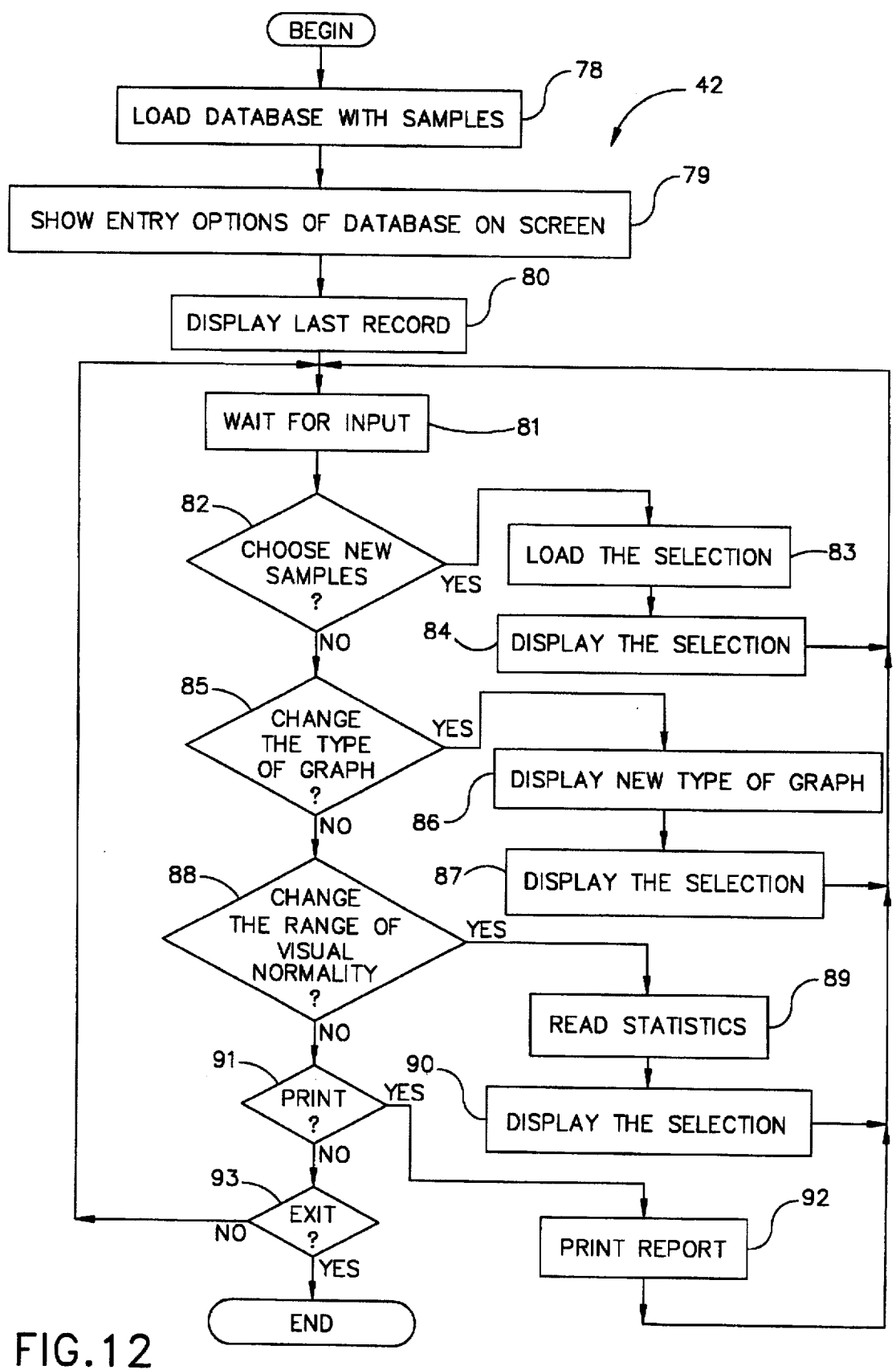
FIG. 12 is a flow chart that illustrates the operations of saving and retrieving data used by the visual performance tester of FIG. 1.

In order to be aware of the test cases earlier registered into the database, the entire local informational database is loaded in the memory of the PC at function block 78 (see FIG. 12), and its "entry options" (e.g., some of the earlier-entered records) are displayed on the screen at function block 79. A graphical representation of the last test will be displayed by function block 80 for the operator's reference.

The operator may select various options at function block 81, as follows: [1] to view graphic display samples of other tests saved in the database (via decision block 82 and function blocks 83 and 84); [2] to change the type of graphic display being used (via decision block 85, and function blocks 86 and 87); [3] to modify the statistical average range of visual normality (via decision block 88, and function block 89 and 90); [4] to print the information retrieved (via decision block 91 and function block 92—see also FIGS. 19, 20 and 21); [5] or to finish (by Exiting) or to continue inspecting results in the database (via decision block 93).

Test Drawing

If a set of test data is currently being displayed on the screen, it can be translated into graphical information at function block 94 (see FIG. 13), based upon samples registered in the database. The system operator is also able to modify the current options at function block 95, as follows: [1] to change the main graphic display (at decision block 96 and function block 97); [2] to change the range of normality used in the graph (at decision block 98 and at function block 99); or [3] to exit without changes (at decision block 100). For examples of the types of graphical data that can be displayed in the preferred embodiment, see FIGS. 19 and 20.

Connection to a Central Database

Figure 14:
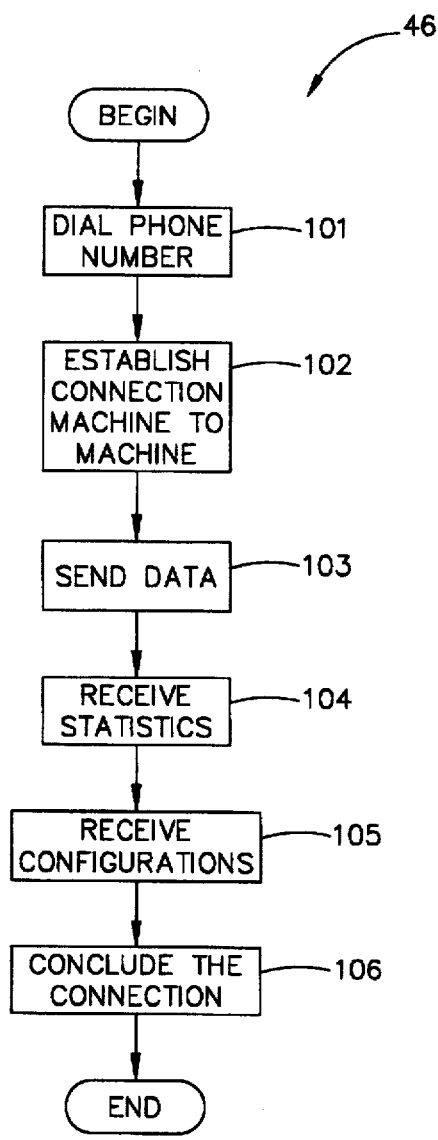
FIG. 14 is a flow chart that shows the operational steps required in connecting the visual performance tester of FIG. 1 to a central database.

In order to gather the maximum information available on various human test subjects (i.e., patients), a central database preferably will be used to contain such information and will be accessible by more than one testing installation. The connection of new modules (i.e., testing installations) are made through dedicated telephone lines using a Modem interface per testing installation. The telephone number of the reference database is dialed at function block 101 (see FIG. 14), and a connection is established between the central database and the computer at the testing installation (e.g., computer 5) at function block 102.

Once a communication link has been established with the central database facility, all the data samples collected until this moment are transmitted under the control of function block 103. The central database then retrieves any new statistical information contained therewithin and transmits it to the testing installation, whereupon the new information is received, as per function block 104. Additionally, the central database transmits the protocols of new available configurations, which are received at the testing installation under the control of function block 105. Finally the connection is concluded at function block 106.

Screen Calibration Module

To calibrate the monitor's screen (see FIG. 15), the screen first is covered completely in white by function block 107. Certain instructional messages are then provided by function block 108 to help the system operator calibrate the "intensity" and "contrast" attributes of the monitor 7 with appropriate values. The system operator now uses the touchscreen to enter commands and responses, as per function block 109. Once the screen is touched (as detected at function block 109), the screen displays a white rectangle with a black background (as per function block 110). After that has occurred, a new set of instructions are given under the control of function block 111 to arrive at the precise measurements that provide identical visual results for all tests at all testing installations. A final touch of the screen ends the calibration process, as per function block 112.

Figure 19A:
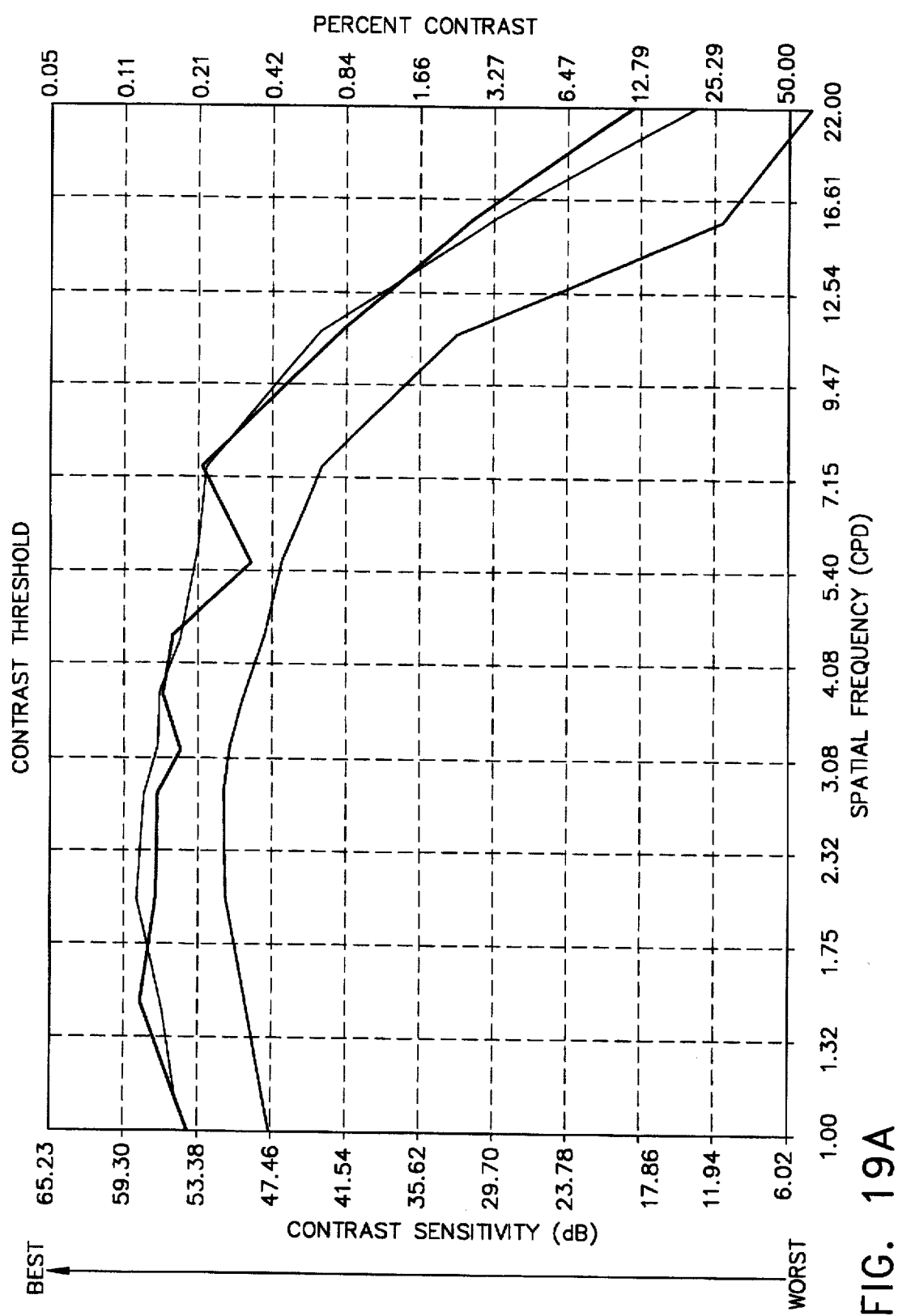
FIGS. 19A–19C are charts depicting the results of a vision test performed by the visual performance tester of FIG. 1.
Figure 19B:
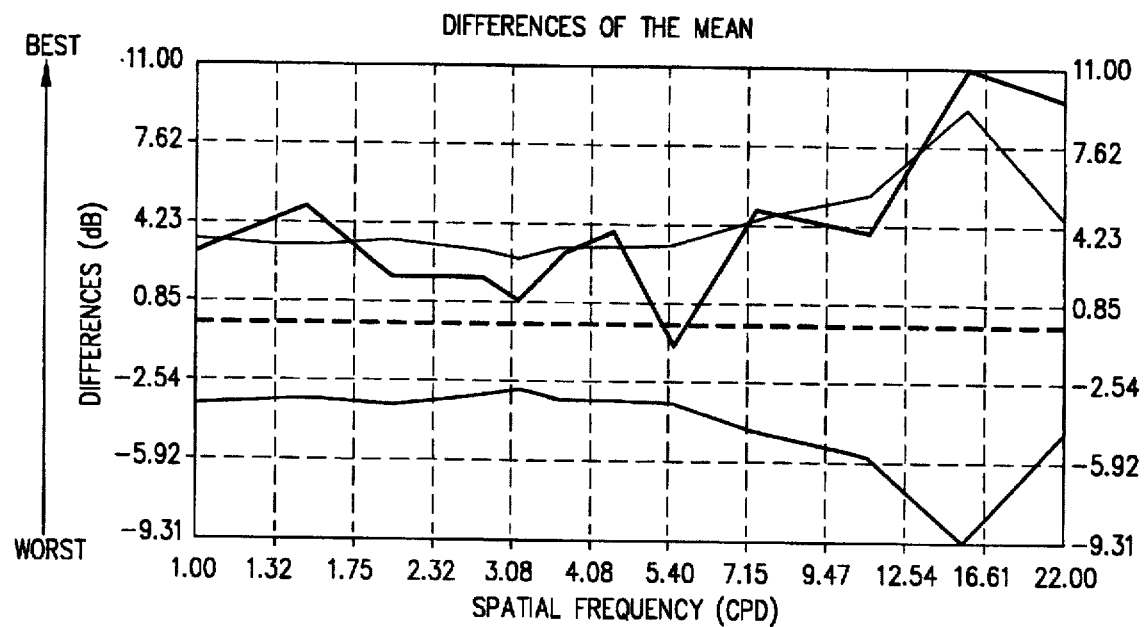
Figure 19C:
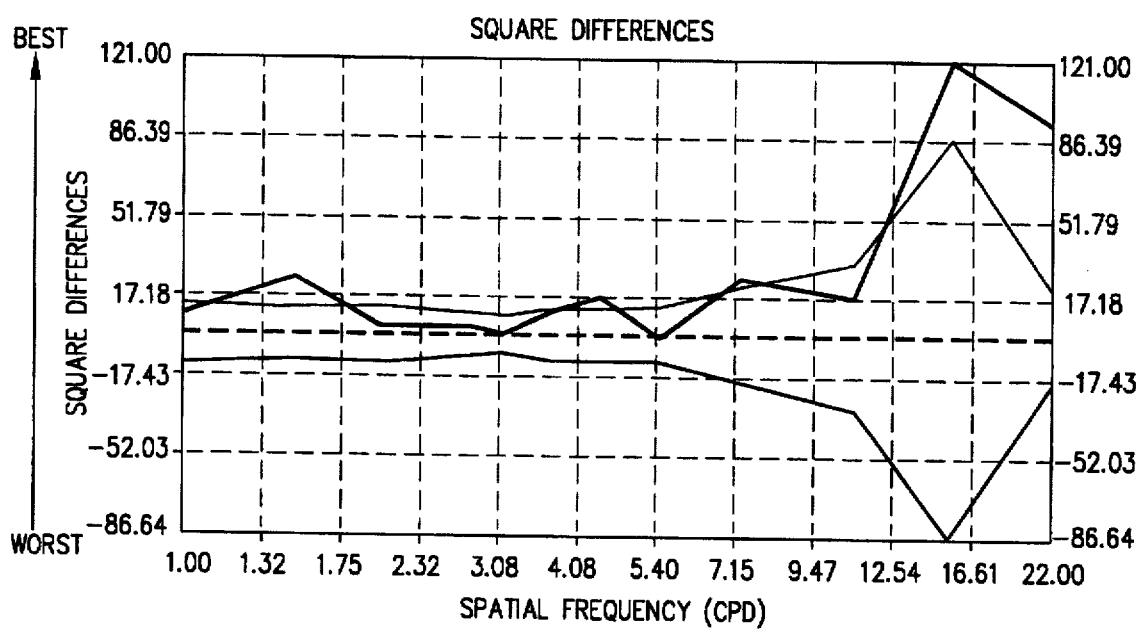

In FIGS. 19A–19C, a patient's "contrast sensibility function" is shown on the main graph. The "gray" band observed in the three charts shows the average range for humans, which preferably corresponds to the standard deviation of a statistically significant sample of previously tested human patients. To be statistically significant, the database should contain a large number of samples (e.g., over 2000), and of course, may potentially contain the entire human population of the world. The two smaller charts show a comparison between the patient's result and the results for the average range of people, in which the left chart contains simple differences and the right chart contains amplified differences.

The patient's data and the information provided by the vision test are given in a verbal report displayed below the charts, and the average range of people used and the loss/gain of vision sensibility information is also given. The quantity known as the "VPT Balance" (shown on FIG. 19 as the number+3.56 dB) is the statistical value given to this patient's test results, thereby providing to the medical professional a "quick" numeric value (or "score") for that patient. A positive number represents a result above average, and a negative number represents a result below average. A zero (0) value represents the average, or more accurately, the statistical mean of the database samples, as accumulated over all spatial frequencies tested (as depicted along the X-axis of the main chart).

Figure 20:
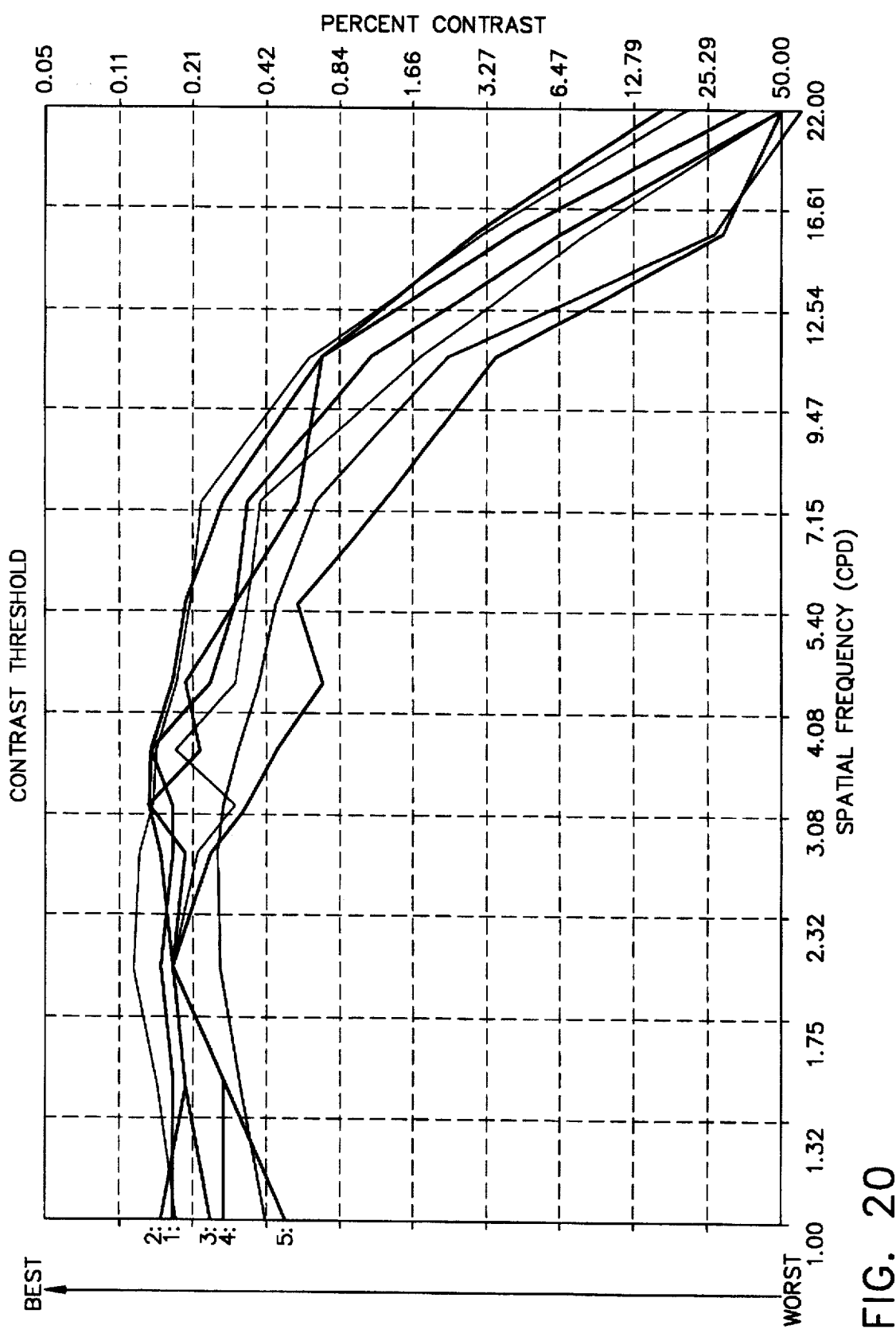
FIG. 20 is a chart showing visual performance test samples of several different patients.
Figure 21:
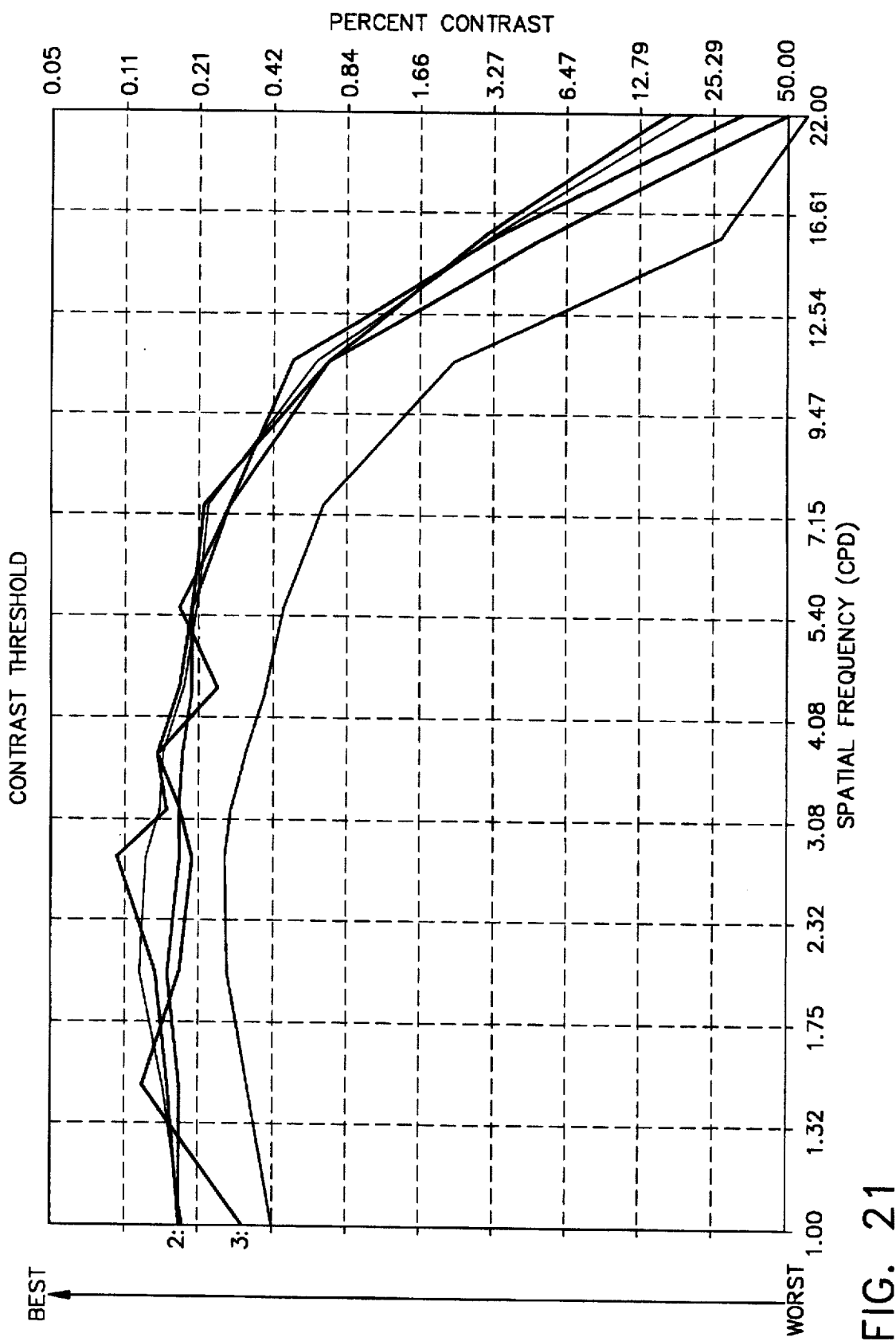
FIG. 21 is a chart that illustrates a comparison of several selected tests using the visual performance tester of FIG. 1. A brief description of each test is given in a verbal report displayed below the chart.

FIG. 20 depicts essentially the same type of graphical information as FIG. 19, however, test results for several individual patients are charted. It will be understood that FIG. 20 could also be showing several results of the same patient, taken at different times. FIG. 21 also shows similar information, however, different types of tests may be displayed upon one graph (as an option). It will be further understood that many types of information in different formats could be displayed on charts, and many types of numeric quantities could be evaluated without departing from the principles of the present invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

I claim:

1. A vision performance tester, comprising:

(a) a processing circuit and a memory circuit which contains software used in controlling a monitor screen, said monitor screen being placed within a domed structure that substantially prevents outside light from reaching said monitor screen, said domed structure including a support device used to position a human patient's eye at a pre-determined distance from said monitor screen, said processing circuit being in communication with a manual input device operable by said patient with which said patient enters responses to visual displays that appear upon said monitor screen;

(b) said processing circuit being configured to display on said monitor screen a successive series of visual test patterns that, if discernible by said patient, will cause said patient to enter a response via said manual input device, said visual test patterns each comprising a circle containing a plurality of parallel dark bands, said bands, from one visual test pattern to another, having a varying inclination and a varying spatial frequency, said successive series of visual test patterns gradually and somewhat randomly decreasing in video contrast so as to determine said patient's critical vision limitations while creating a data profile of test results concerning this patient; and (c) said processing circuit being further configured to compare said data profile to a database of accumulated vision test data that represents normalized human eye responses, the results of said comparison being presentable in a form easily understood by a medical profession that assists in a diagnosis of potential vision problems.

2. The vision performance tester as recited in claim 1, wherein said domed structure comprises an interior non-reflective surface.

3. The vision performance tester as recited in claim 1, wherein said results of the comparison between said data profile and said database of accumulated vision test data are in a graphical format.

4. The vision performance tester as recited in claim 1, wherein said bands comprise gray tonalities.

5. The vision performance tester as recited in claim 1, wherein said bands exhibit multiple configurations by varying, from one visual test pattern to another, at least one of the following characteristics: (a) color, (b) width, and (c) number.

6. The vision performance tester as recited in claim 1, wherein the patient's "threshold" minimum perceivable contrast capability is determined by the value of the video contrast of said bands one level above that contrast level at which the patient cannot discern the bands.

7. A method of testing a human patient's vision limitations, said method comprising the steps of:

(a) providing a processing circuit and a memory circuit which contains software used in controlling a monitor screen, said monitor screen being placed within a domed structure that substantially prevents outside light from reaching said monitor screen, said domed structure including a support device used to position a human patient's eye at a pre-determined distance from said monitor screen, said processing circuit being in communication with a manual input device operable by said patient with which said patient enters responses to visual displays that appear upon said monitor screen;

displaying on said monitor screen a successive series of visual test patterns that, if discernible by said patient, will cause said patient to enter a response via said manual input device, said visual test patterns each comprising a circle containing a plurality of parallel dark bands, said bands, from one visual test pattern to another, having a varying inclination and a varying spatial frequency, said successive series of visual test patterns gradually and somewhat randomly decreasing in video contrast so as to determine said patient's critical vision limitations while creating a data profile of test results concerning this patient; and (c) comparing said data profile to a database of accumulated vision test data that represents normalized human eye responses, the results of said comparison being presentable in a form easily understood by a medical profession that assists in a diagnosis of potential vision problems.

8. The method as recited in claim 7, wherein said results of the comparison between said data profile and said database of accumulated vision test data are in a graphical format.

9. The method as recited in claim 7, further comprising the step of measuring the amount of time between the presentation of a new visual test pattern upon said monitor screen and the entering of a response by said patient via said manual input device.

10. The method as recited in claim 7, wherein said bands comprise gray tonalities.

11. The method as recited in claim 7, wherein said bands exhibit multiple configurations by varying, from one visual test pattern to another, at least one of the following characteristics: (a) color, (b) width, and (c) number.

12. The method as recited in claim 7, wherein said sub-step of determining the patient's critical vision limitations comprises finding the value of the video contrast of said bands one level above that contrast level at which the patient cannot discern the bands.

13. The method as recited in claim 7, wherein said sub-step of the patient entering a response via said manual input device comprises: touching the appropriate one of at least three different areas of said monitor screen depending upon the inclination of said bands being presently displayed on that monitor screen.

* * * * *